US007198702B1

(12) United States Patent
Washizu et al.

(10) Patent No.: US 7,198,702 B1
(45) Date of Patent: Apr. 3, 2007

(54) METHOD FOR SEPARATING SUBSTANCES USING DIELECTROPHORETIC FORCES

(75) Inventors: Masao Washizu, Kyoto-fu (JP); Tomohisa Kawabata, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 69 days.

(21) Appl. No.: 09/670,399

(22) Filed: Sep. 27, 2000

(30) Foreign Application Priority Data

Sep. 30, 1999 (JP) ................................ 11/279912

(51) Int. Cl.

| | |
|---|---|
| ***B01D 57/02*** | (2006.01) |
| ***G01N 27/447*** | (2006.01) |
| ***G01N 33/53*** | (2006.01) |
| ***G01N 33/543*** | (2006.01) |
| ***G01N 33/566*** | (2006.01) |
| ***G01N 1/10*** | (2006.01) |
| ***G01N 35/08*** | (2006.01) |
| ***G01N 37/00*** | (2006.01) |
| ***B03C 5/00*** | (2006.01) |
| ***C12N 15/09*** | (2006.01) |
| ***C12Q 1/68*** | (2006.01) |
| *C12M 1/00* | (2006.01) |

(52) U.S. Cl. ...................... 204/547; 204/450; 204/600; 204/643

(58) Field of Classification Search ................ 204/600, 204/450, 547, 247, 601, 643
See application file for complete search history.

(56) References Cited

U.S. PATENT DOCUMENTS

| | | | | |
|---|---|---|---|---|
| 4,970,154 | A * | 11/1990 | Chang | 424/93.21 |
| 5,277,774 | A * | 1/1994 | Shmidt et al. | 204/545 |
| 5,344,535 | A * | 9/1994 | Betts et al. | 204/547 |
| 5,569,367 | A * | 10/1996 | Betts et al. | 204/547 |
| 5,585,248 | A * | 12/1996 | Ashida et al. | 435/15 |
| 5,626,734 | A * | 5/1997 | Docoslis et al. | 204/547 |
| 5,653,859 | A * | 8/1997 | Parton et al. | 204/450 |
| 5,814,200 | A * | 9/1998 | Pethig et al. | 204/547 |
| 5,948,328 | A * | 9/1999 | Fiedler et al. | 264/5 |
| 5,958,202 | A * | 9/1999 | Regnier et al. | 204/451 |
| 5,993,631 | A * | 11/1999 | Parton et al. | 204/547 |
| 6,080,556 | A * | 6/2000 | Sugiyama et al. | 435/69.1 |
| 6,133,436 | A * | 10/2000 | Koster et al. | 502/233 |
| 6,149,789 | A * | 11/2000 | Benecke et al. | 204/547 |
| 6,171,865 | B1 * | 1/2001 | Weigl et al. | 422/81 |
| 6,221,654 | B1 * | 4/2001 | Quake et al. | 435/286.5 |
| 6,251,691 | B1 * | 6/2001 | Seul | 436/534 |
| 6,294,063 | B1 * | 9/2001 | Becker et al. | 204/450 |
| 6,387,707 | B1 * | 5/2002 | Seul et al. | 436/164 |
| 6,875,329 | B2 * | 4/2005 | Washizu et al. | 204/547 |
| 2001/0047941 | A1 * | 12/2001 | Washizu et al. | |

FOREIGN PATENT DOCUMENTS

| | | |
|---|---|---|
| EP | 0 815 942 A1 | 1/1998 |
| JP | 5126796 | 5/1993 |

OTHER PUBLICATIONS

Washizu and Kurosawa, "Electrostatic Manipulation of DNA in Microfabricated Structures", IEEE Transactions on Industry Applications, vol. 26, No. 6, Nov./Dec. 1990.*

Washizu M. et al.: "Molecular Dielectrophoresis of Biopolymers"; IEEE Transactions of Industry Applications, IEEE Inc.; vol. 30, No. 4, Jul. 1, 1994; pp. 835-843.

J. Price et al.: "Application of a new optical technique for measuring the dielectrophoretic behavior of micro-organisms"; Biochimica et Biophysica Acta, 964 (1988), pp. 221-230.

* cited by examiner

*Primary Examiner*—Anthony J. Green
(74) *Attorney, Agent, or Firm*—Armstrong, Kratz, Quintos, Hanson & Brooks, LLP

(57) ABSTRACT

The present invention has an object of providing a method by which two kinds or more of molecules can be separated each other by using dielectrophoretic forces. The present invention comprises two methods. The first method is a method comprising forming a complex substance of a "specific molecule" containing in a sample, and a "substance capable of changing dielectrophoretic properties of the specific molecule", which binds to the "specific molecule" contained therein, and thereby separating the complex substance and the molecules other than the specific molecule in the sample from each other. The second method is a method comprising placing a solution in which two kinds or more of molecules are dissolved under a strong electric field strength, that is, under a nonuniform electric field having an electric field strength of 500 KV/m or higher, by using dielectrophoretic forces.

22 Claims, 9 Drawing Sheets

METHOD FOR SEPARATING SUBSTANCES USING DIELECTROPHORETIC FORCES

BACKGROUND OF THE INVENTION

1. Field of the Invention

The present invention relates to methods for separating two or more kinds of molecules using dielectrophoretic forces.

2. Background of the Invention

Recently, advance in semiconductor technology has established processing technology of materials at scales of nanometer to micrometer by means of micromachining technology such as photolithography, which continues to make advance also at the present.

In the fields of chemistry and biochemistry, new technology called a Micro Total Analysis System (μ-TAS), Laboratory on a chip is growing, in which such micromachining technology is employed to carry out a whole series of chemical/biochemical analytical steps of extraction of component(s) to be analyzed from biological samples (extraction step), analysis of the component(s) with chemical/biochemical reaction(s) (analysis step), and subsequent separation (separation step) and detection (detection step) using a highly small analytical device integrated on a chip having each side of a few centimeters to a few ten centimeters in length.

Procedures of the μ-TAS are expected to make a large contribution to saving the analyzing time, reducing the amounts of samples to be used and reagents for chemical/biochemical reactions, and reducing the size of analytical instruments and the space for analysis in the course of all the chemical/biochemical analytical steps.

For the separation step in μ-TAS, in particular, there have been developed capillary electrophoretic methods in which a capillary (fine tube) with an inner diameter of less than 1 mm which is made of Teflon, silica, or the like as material is used as the separating column to achieve separation with charge differences of substances under a high electric field, and capillary column chromatographic methods in which a similar capillary is used to achieve separation with the difference of the interaction between carrier in the column medium and substances.

However, capillary electrophoretic methods need a high voltage for separation and have a problem of a low sensitivity of detection due to a limited capillary volume in the detection area and also these is found such a problem that they are not suitable for separation of high molecular weight substances, though suitable for separation of low molecular weight substances, since the length of capillary for separation is limited on the capillary chip on a chip and thus a capillary can not be made into a length enough for separating high molecular weight substances. In addition, in capillary column chromatographic methods there is a limit in making the throughput of separation processing higher and also these is such a problem that reducing the processing time is difficult.

Thus, one means to solve problems as described above are now noticed separation methods utilizing the phenomenon in which the placement of substances under a nonuniform electric field results in the positive and negative polarization within the substances, thereby providing a driving force of moving the substances, so-called dielectrophoretic force [H. A. Pohl, "Dielectrophoresis", Cambridge Univ. Press (1978); T. B. Jones, "Electromechanics of Particles", Cambridge Univ. Press (1995), and the like].

These separation methods are presently believed to be the most suitable separation method in m-TAS from the following points: (1) a rapid separation can be expected at a low applied voltage without requiring a high voltage as in capillary electrophoresis, since an electric field and its gradient can be increased to an extreme extent if micromachined electrodes are employed, because the degree of dielectrophoretic forces depends on the size and dielectric properties of substances (particles) and is proportional to the electric field gradient; (2) an increase in temperature due to applying the electric field can be minimized, and a high electric field can be formed, since a strong electric field area is localized at a significantly small region; (3) as the dielectrophoretic force is a force proportional to the electric field gradient, the force is understood as independent on the polarity of the applied voltage, and thus works under an AC electric field in a similar way to a D.C. electric field, and therefore if a high frequency A.C is employed, an electrode reaction (electrolytic reaction) in an aqueous solution can be suppressed, so that the electrodes themselves can be integrated in the channel (sample flow path); (4) improvement in a detection sensitivity can be expected, since there is no restriction to a chamber volume of the detection component as in capillary electrophoresis, and the like.

As separation methods utilizing dielectrophoretic forces as described above, there have been reported various methods until now [M. Washizu, et. al., IEEE Transaction IA, vol. 30, No. 4, pp. 835–843 (1994); M. Washizu, et. al., Conf. Rec. The Institute of Electrostatics Japan, '93 Ann. Meet. (Int'l Session), pp. 27–32 (1993); Y. Huang, et al., Biophys. J., vol. 73, pp. 1118–1129 (1997); and N. G. Green et al., J. Phys. D.: Appl. Phys. vol. 31, 25–30 (1998), and the like].

For example, Journal of Physics D, British Journal of Applied Physics (J. Phys. D: Appl. Phys.), 27, 2659–2662 (1994) describes that from suspensions containing HL-60 cells and normal blood cells, respective cells can be separated; Microbiology, 140, 585–591 (1994) describes that from suspensions containing different microorganisms, the microorganisms can be separated into different species of yeast and bacteria from one another; Journal of Biotechnology, 32, 29–37 (1994) describes that from suspensions containing living and dead cells of yeast, both cells can be separated from each other; and J. Phys. D: Appl. Phys., 31, 25–30 (1998) describes that from suspensions containing latex particles having a diameter of 93 nm and 216 nm, both particles can be separated by dielectrophoresis and electro-fluid forces from each other.

Additionally, M. Washizu, et al., IEEE Transaction IA, vol. 30, No. 4, pp. 835–843 (1994) reported that using solutions containing a single biological component as samples, the component for example, avidin (68 kDa), concanavalin A (52 kDa), chymotrypsinogen A (25 kDa), or ribonuclease A (13.7 kDa)] is captured on the electrode by dielectrophoretic forces, and also using solutions containing a single biological component as samples, the component can be captured on the electrode by dielectrophoretic forces [the capture ratio was 100% when using a sample of 48.5 kb DNA alone, about 60% when using a sample of 15 kb DNA alone, about 50% when using a sample of 9 kb circular DNA alone, and a few % using a sample of avidin (68 kDa) alone].

However, reports on separation methods with conventional dielectrophoretic forces as described above are limited to separating particles having a low solubility in a solution, relative to DNAs and proteins, such as various cells and latex particles, or otherwise only capturing a single (one kind of) DNA or protein, and any report has not been presented yet on separation of respective molecules from solutions in which are dissolved two or more kinds of biological component molecules, in particular, such as for example DNAs and proteins.

This is because two kinds or more of molecules such as proteins and DNAs, which have a very small physical size, as compared with cells and latex particles, are considered to be difficult in separation from each other from solution in which those molecules are dissolved on the basis of the difference between the size of respective molecules by using dielectrophoretic forces, since the strength of dielectrophoretic forces depends on the physical size of substances, so that substances having a larger volume will receive a larger dielectrophoretic force, and also because conventional separation has been carried out at a weak electric field strength lower than 500 KV/m, whereby separation is not achievable.

SUMMARY OF THE INVENTION

It is an object of the present invention to provide a method for separating two or more kinds of molecules each other by using dielectrophoretic forces.

It is also an object of the present invention to provide a method for separating each other two or more kinds of molecules dissolved in a solution, by using dielectrophoretic forces, such separation having so far been impossible.

Furthermore, it is an object of the present invention to provide a method capable of rapidly and readily separating respective molecules from a solution in which are dissolved two or more kinds of molecules, for example, biological component molecules such as DNAs and proteins, such separation having so for been impossible by dielectrophoretic forces.

The present invention is carried out for purpose of solving the above mentioned problems and, for the first time, has achieved the successful separation of two or more kinds of molecules, such separation having so for been impossible by using dielectrophoretic forces by means of two types of methods described below.

The first method comprises forming a complex substance of a "specific molecule" in a sample and a "substance capable of changing dielectrophoretic properties of the 'specific molecule' which binds to the 'specific molecule' contained therein" and thereby separating the complex substance and the molecules other than the specific molecules in the sample from each other. In so far know separation methods with dielectrophoretic forces, separation has not facilitated at all by forming such a complex substance, and such an idea has not recognized at all in the past.

The second method comprises placing a solution in which two or more kinds of molecules, in particular, for example, biological component molecules such DNAs and proteins are dissolved under a strong electric field, that is, a nonuniform electric field having an electric field strength of 500 KV/m or higher. It is a new finding unknown to date that respective molecules can be separated each other by such a method.

Therefore, the present invention relates to: (1)(a) a method for separating a complex substance of a "specific molecule" in a sample and a "substance capable of changing dielectrophoretic properties of the specific molecule" which binds to the "specific molecule" from molecules other than the "specific molecule" in the sample, comprising forming the complex substance of the "specific molecule" and the "substance capable of changing dielectrophoretic properties of the specific molecule", and applying the resulting reaction mixture containing the complex substance to dielectrophoresis, and separating the complex substance from molecules other than the "specific molecule"; and a method for measuring the "specific molecule" in the separated complex substance or a molecule other than the "specific molecule" in the sample; and (b) a method for separating a complex substance of a "specific molecule" in a sample, a "substance binding to the specific molecule" and a "substance capable of changing dielectrophoretic properties of the specific molecule" which binds to the "specific molecule" from the "substance binding to the specific molecule" which is not involved in forming the complex substance, comprising contacting the sample containing the "specific molecule" with the "substance binding to the specific molecule", and the "substance capable of changing dielectrophoretic properties of the specific molecule" to form the complex substance, and applying the resulting reaction mixture containing the complex substance to dielectrophoresis, and separating the complex substance from the "substance binding to the specific molecule" which is not involved in forming the complex substance; and (c) a method for determining an amount of a component in a sample, comprising contacting a sample containing a "specific molecule" with a "specific molecule labeled by a labeling substance", and a "substance capable of changing dielectrophoretic properties of the specific molecule" which binds to the "specific molecule" to form a labeled complex substance of the "specific molecule labeled by the labeling substance" and the "substance capable of changing dielectrophoretic properties of the specific molecule", applying the resulting reaction mixture containing the labeled complex substance to dielectrophoresis, separating the labeled complex substance from the "specific molecule labeled by the labeling substance" which is not involved in forming the complex substance, measuring the "specific molecule labeled by the labeling substance" in the separated labeled complex substance or the "specific molecule labeled by the labeling substance" which is not involved in forming the complex substance, and determining an amount of the component in the sample on the basis of the measurement result; and (d) a kit for measuring a component in a sample for use in methods (a) to (c), comprising a "substance capable of changing dielectrophoretic properties of the specific molecule" in the sample, which can form a complex substance with the "specific molecule"

In addition, the present invention relates to (2) method for separating two or more kinds of molecules, each other which comprises placing a solution in which the two or more kinds of molecules are dissolved under a nonuniform electric field having an electric field strength of 500 KV/m or higher, formed by electrodes which have a structure capable of forming a nonuniform electric field.

More specifically, the present invention relates to a method for detecting a molecule to be measured in a sample, which comprises reacting a liquid sample, in which a "molecule to be measured" is dissolved, and a solution, in which a "substance specifically binding to the molecule to be measured" is dissolved, to obtain a solution in which a complex substance of the "molecule to be measured" and the "substance specifically binding to the molecule to be measured", and the "substance specifically binding to the molecule to be measured" which is not involved in the reaction are dissolved, placing the solution under a nonuniform electric field having an electric field strength of 500 KV/m or higher, the field being formed by electrodes which have a structure capable of forming a horizontally and vertically ununiform electric field, separating the complex substance from the "substance specifically binding to the molecule to be measured" which is not involved in the reaction, and measuring the "substance specifically binding to the molecule to be measured" in the complex substance, or the "substance specifically binding to the molecule to be measured" which is not involved in the reaction; and a method for measuring a substance to be measured in a sample comprising, reacting a liquid sample containing a "molecule to be measured", a "molecule to be measured labeled by a labeling substance", and a "substance specifically binding to the molecule to be measured" to obtain a solution containing a complex substance of the "molecule to be measured labeled by a labeling substance" and the "substance specifically binding to the molecule to be measured", a complex substance of the "molecule to be measured" and the "substance specifically binding to the molecule to be measured", and the "molecule to be measured labeled by a labeling substance which is not involved in the reaction, placing the obtained solution under a nonuniform electric field having an electric field strength of 500 KV/m or higher, the field being formed by electrodes which have a structure capable of forming a horizontally and vertically ununiform electric field, separating the complex substance of the "molecule to be measured labeled by a labeling substance" and the "substance specifically binding to the molecule to be measured" from the "molecule to be measured labeled by a labeling substance" which is not involved in forming the complex, and then measuring the "molecule to be measured labeled by a labeling substance" in the complex substance or the "molecule to be measured labeled by a labeling substance which is not involved in forming the complex substance to determine the amount of the molecule to be measured in the sample based on the results.

The above and other objects and advantages of the invention will become more apparent from the following description.

DETAILED DESCRIPTION OF THE PREFERED EMBODIMENT

Embodiments of the present invention will be described as follows.

Dielectrophoresis forces are forces resulting from the phenomenon described below.

Figure 1:
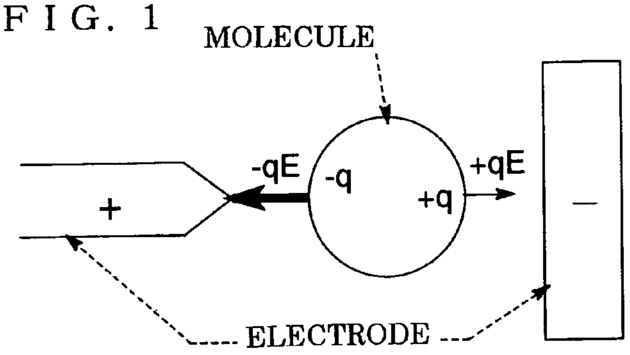
FIG. 1 is a representation showing the principle of dielectrophoresis.

Namely, as shown in FIG. 1, a neutral molecule placed in an electric field has a positively induced polarization charge +q downstream the electric field and a negatively induced polarization charge −q upstream the electric field, respectively, thus +q receives a force of +qE from the electric field E and this portion is pulled downstream in the electric field, whereas −q receives a force of −qE from the electric field E and this portion is pulled upstream in the electric field. If the molecule is neutral, +q and −q have an equal absolute value, and if the electric field is uniform regardless of the positions, both received forces are balanced, therefore the molecule does not move. However, in the case where the electric field is nonuniform as shown in FIG. 1, an attractive force toward a strong electric field becomes larger, thus the molecule is driven toward the strong side of the electric field. This phenomenon in which neutral molecules move under a nonuniform electric field is called dielectrophoresis (DEP), and the force received by molecules during that time is called dielectrophoretic force. If molecules are charged ones, the moving mode is such one as comprising electrophoretic forces in addition to dielectrophoretic forces.

Samples to which the present invention can be applied include samples derived from living body such as body fluids including serum, plasma, cerebrospinal fluid, synovial fluid, lymph, etc., excreta including urine, feces, etc., and treated materials thereof. Treated materials include diluted solutions of these samples derived from a living body in water, buffers, or the like, or those reconstituted by appropriately dissolving or suspending molecules as described below from these body-derived samples in water, buffers, or the like. Samples to which the present invention is applied also include those containing the above described molecules which are chemically synthesized.

The first method according to the present invention (hereinafter sometimes abbreviated as embodiment ①), relates to a method for separating a specific molecule in such a sample as above from other co-existing molecules, and additionally, determining the separated molecule, and a kit for use in such a method.

Such embodiments of the present invention encompass: (a) one characterized by forming a complex substance of a "specific molecule in a sample" and a "substance capable of changing dielectrophoretic properties of the specific molecule" which binds to the "specific molecule", (b) one characterized by forming a complex substance of a "specific molecule in a sample", a "substance binding to a specific molecule", and a "substance capable of changing dielectrophoretic properties of the specific molecule" which binds to the "specific molecule", and (c) one characterized by forming a complex substance of either a "specific molecule" in a sample or a "specific molecule labeled by a labeling substance" and a "substance capable of changing dielectrophoretic properties of the specific molecule" which binds to the "specific molecule", and the like.

In each of these embodiments, a "specific molecule" includes a molecule intended to measure (also referred to a molecule to be measured) and a molecule other than a molecule intended to measure (also referred to a molecule not to be measured).

Specific molecules (molecules to be measured) include, for example, nucleotide chains (oligonucleotide chains, polynucleotide chains), chromosomes, peptide chains (for example, C-peptide, angiotensin I, and the like), proteins (for example serum proteins such as immunoglobulin A (IgA), immunoglobulin E (IgE), immunoglobulin G (IgG), $\beta_2$-microglobulin, albumin, and ferritin; enzyme proteins such as amylase, alkaline phosphatase, and γ-glutamyltransferase; antiviral antibodies to viruses such as Rubella virus, Herpes virus, Hepatitis virus, ATL virus, and AIDS virus and antigenic substances derived from these viruses; antibodies to various allergens; lipids such as lipoproteins; and proteases such as trypsin, plasmin and serine proteases); sugar chains (for example, sugar chains of α-fetoprotein, CA19-9, prostate-specific antigen, carcinoembryonic antigen, substances having particular sugar chains produced by cancer cells), lectins (for example, concanavalin A, *Lens culinaris* lectin, *Phaseolus vulgaris* lectin, *Dutura stramonium* lectin, wheat germ lectin) and the like.

Additionally, specific molecules (molecules to be measured) also include molecules existing as two or more kinds of substances having the same function or molecules existing as two or more kinds of substances having a similar structure but having a different function such as isozymes and hormones, for example, enzymes such as amylase, alkaline phosphatase, acid phosphatase, γ-glutamyltransferase (γ-GTP), lipase, creatine kinase (CK), lactate dehydrogenase (LDH), glutamic-oxaloacetic transaminase (GOT), glutamic-pyruvic transaminase (GPT), renin, protein kinases, tyrosine kinases; physiologically active substances such as steroid hormones, human chorionic gonadotropin (hCG), prolactin, thyroid-stimulating hormone (TSH), luteinizing hormone (LH); cancer associated antigens such as prostate-specific antigen (PSA), $\alpha^2$-macroglobulin, carcinoembryonic antigen (CEA), α-fetoprotein, and the like.

A "substances capable of changing dielectrophoretic properties" in the present invention (also referred to a separation improving substance) includes a substance which, by binding to a specific molecule (molecule to be measured) to form a complex with the specific molecule, causes differences in behavior to dielectrophoretic operation between the specific molecule and the other co-existing substances (molecules not to be measured, for example, one or more kinds of substances which are not involved in the formation of the complex): for example 1) a substance which can cause a result that any one of both is captured on the dielectrophoresis electrode and the others are not captured, and more specifically, a substance which can provide changes in the movement speed of the specific molecule and the other co-existing substances, for example, in the case of employing a so-called dielectrophoretic chromatography apparatus (Field Flow Fractionation apparatus) in which separation is carried out as described below with the interaction between dielectrophoretic forces caused by the molecules in the electric field and the molecular movement, and more preferably, a substance by which any one of these can be captured on the electrode and the others can be passed through on the dielectrophoresis electrode without being captured on the electrode; or 2) a substance which can cause a result that any one of both receives negative dielectrophoretic forces and the others receive positive dielectrophoretic forces, and more specifically, a substance which, for example, can allow only the specific molecule to gather at a particular position on the dielectrophoretic electrode, and more preferably, a substance which can allow any one of these to gather at a strong electric field strength region on the dielectrophoresis electrode by positive dielectrophoretic forces and the others to gather at a weak electric field strength region on the dielectrophoresis electrode by negative dielectrophoretic forces; or the like.

Such a substance includes inorganic metal oxides such as silica and alumina; metals such as gold, titanium, iron, and nickel; inorganic metal oxides and the like having functional groups introduced by silane coupling process and the like; living things such as various microorganisms and eukaryotic cells; polysaccharides such as agarose, cellulose, insoluble dextran; synthetic macromolecular compounds such as polystyrene latex, styrene-butadiene copolymer, styrene-methacrylate copolymer, acrolein-ethylene glycol dimethacrylate copolymer, styrene-styrenesufonate latex, polyacrylamide, polyglycidyl methacrylate, polyacrolein-coated particles, crosslinked polyacrylonitrile, acrylic or acrylic ester copolymer, acrylonitrile-butadiene, vinyl chloride-acrylic ester and polyvinyl acetate-acrylate; biological molecules such as erythrocyte, sugars, nucleic acids, proteins and lipids, and the like.

These substances are usually used in the form of fine particles to granules.

A "substance binding to a specific molecule" which can be used in the present invention may not be limited in particular and includes a substance which, from a "specific molecule" in a sample, can form a complex substance of the "specific molecule", a "substance binding to the specific molecule" and a "specific substance capable of changing dielectrophoretic properties", and does not substantially form a complex substance of "molecules other than the specific molecule", the "substance binding to the specific molecule" and the "specific substance capable of changing dielectrophoretic properties". In short, so long as the substance does not form the latter complex substance of the above-mentioned three substances, it can be used for this purpose even if it binds to molecules other than the "specific molecule". Actually, a "substance specifically binding to the specific molecule" is preferably used.

A "substance binding to a specific molecule" refers to a substance binding to a "specific molecules" by mutual reactions such as an "antigen"-"antibody" reaction, a "sugar chain"-"lectin" reaction, an "enzyme"-"inhibitor" reaction and a "protein"-"peptide chain" reaction, a "chromosome or nucleotide chain"-"nucleotide chain" reaction. If one partner is a specific molecule (molecule to be measured) in each combination described above, the other is a "substance binding to a specific molecule (molecule to be measured)" as described above. For example, if a specific molecule (molecule to be measured) is an "antigen", a "substance binding to the specific molecule (molecule to be measured)" is an "antibody", and if a specific molecule (molecule to be measured) is an "antibody", a "substance binding to the specific molecule (molecule to be measured)" is an "antigen" (other combinations described above have a similar relationship).

It is suitable that the "substance binding to the specific molecule (molecule to be measured)" binds at least to the "specific molecule", and it does not necessarily specifically bind only to the specific molecule. However, in the case where a "substance binding to the specific molecule (molecule to be measured)" is not a substance which does not specifically bind to the specific molecule, the "substance capable of changing dielectrophoretic properties of the specific molecule" to be used in the combination is generally one binding specifically to the "specific molecule", or one having properties of binding specifically to a new site formed by forming a complex substance of the "specific molecule" and the "substance binding to the specific molecule (molecule to be measured)".

Such a "substance binding to the specific molecule (molecule to be measured)" is generally one which can be measured (detected) or labeled by a labeling substance by some method. The use of a substance having such a property will make it possible to measure (detect) a specific molecule (molecule to be measured) in a sample. In the case where a specific molecule (molecule to be measured) itself can be detected by some method (for example, an enzyme or the like), or where a specific molecule (molecule to be measured) can bind directly to a labeling substance without (via) a "substance binding to the specific molecule", the specific molecule (molecule to be measured) in a sample can be measured (detected), even if the "substance binding to the specific molecule" possesses no such a property described above, or the "substance binding to the specific molecule" is not employed. Examples as can be detected itself by some method are enzymes, dyes, fluorescent substances, luminescent substances, substances having absorption in the ultraviolet region, and the like.

Labeling substances which can be used in the present invention are any substances usually used in the art, including enzyme immunoassay (EIA), radioimmunoassay (RIA), fluoroimmunoassay (FIA), hybridization, and the like, and they are examplified by enzymes such as alkaline phosphatase (ALP), β-galactosidase (β-Gal), peroxidase (POD), microperoxidase, glucose oxidase (GOD), glucose-6-phosphate dehydrogenase (G6PDH), malate dehydrogenase and luciferase; dyes such as Coomassie Brilliant Blue R250 and methyl orange; radioisotopes such as $^{99m}$Tc, $^{131}$I, $^{125}$I, $^{14}$C, $^{3}$H, $^{32}$P and $^{35}$S; fluorescent substances such as fluorescein, rhodamine, dansyl, fluorescamine, coumarin, naphthylamine or their derivatives and europium (Eu); luminescent substances such as luciferin, isoluminol, luminol and bis(2,4,6-trifluorophenyl) oxalate; substances having absorption in the ultra-violet region such as phenol, naphthol, anthracene and their derivatives; substances having properties as spin labeling agents exemplified by compounds with oxyl groups such as 4-amino-2,2,6,6-tetramethylpiperidine-1-oxyl, 3-amino-2,2,5,5-tetramethylpyrroridine-1-oxyl and 2,6-di-t-butyl-α-(3,5-di-t-butyl-4-oxo-2,5-cyclohexadien-1-ylidene)-p-tolyloxyl, and the like.

Labeling of a specific molecule (molecule to be measured) or a "substance binding to the specific molecule" by a labeling substance can be performed by any one of usual methods commonly used in the art, such as known labeling methods commonly employing in EIA, RIA, FIA, hybridization, or the like, which are known per se [for example, Ikagaku Zikken Koza (Methods in Medical and Chemical Experiments) vol. 8, Edited by Y. Yamamura, 1st ed., Nakayama-Shoten, 1971; A. Kawao, Illustrative Fluorescent Antibodies, 1st ed., Softscience Inc., 1983; Enzyme Immunoassy, Edited by E. Ishikawa, T. Kawai, and K. Miyai, 3rd. ed., Igaku-Shoin, 1987; Molecular Cloning: A Laboratory Manual, 2nd. ed., J. Sambrook, E. F. Fritsch, and T. Maniatis, Cold Spring Harbor Laboratory Press, and the like], and usual methods employing a reaction of avidin (or streptavidin) and biotin.

In the above-mentioned embodiment (a), in order to form a complex substance of a "specific molecule in a sample" and a "substance capable of changing dielectrophoretic properties of the specific molecule", a sample containing a "specific molecule" and a "substance capable of changing dielectrophoretic properties of the specific molecule" are dissolved, dispersed, or suspended, respectively, for example, in water or buffers such as tris(hydroxymethylaminomethane) buffers, Good's buffers, phosphate buffers, borate buffers and the like to give liquid materials, and the liquid materials are mixed and contacted with one another. These sample and substances may be dissolved, dispersed or suspend at once. In the case where a sample containing a "specific molecule" is liquid, a "substance capable of changing dielectrophoretic properties of the specific molecule" can be directly mixed with the sample.

The formation of a complex in the above-mentioned embodiments (b) and (c) of the present invention can also be performed in a similar way as described above.

In the above-mentioned embodiment (b), in order to form a complex substances of a "specific molecule in a sample", a "substance binding to the specific molecule", and a "substance capable of changing dielectrophoretic properties of the specific molecule", a sample containing a "specific molecule", a "substance binding to the specific molecule", and a "substance capable of changing dielectrophoretic properties of the specific molecule" can be dissolved, dispersed, or suspended, respectively, for example, in water or buffers such as tris(hydroxymethylaminomethane) buffers, Good's buffers, phosphate buffers, borate buffers and the like to give liquid materials, and the liquid materials are mixed and contacted with one another. These sample and substances may be dissolved, dispersed or suspend at once. Alternatively, a complex substance of a "substance binding to the specific molecule" and a "substance capable of changing dielectrophoretic properties of the specific molecule" is formed at first in a similar way as described above, and then a liquid material containing the complex substance is further mixed and contacted with a liquid material of a sample containing a specific molecule prepared as described previously. Alternatively, a sample containing a "specific molecule" and a "substance capable of changing dielectrophoretic properties of the specific molecule" are contacted with each other to form a complex substance of these and the resultant is then contacted, with a "substance binding to the specific molecule".

If a sample containing a "specific molecule" is liquid, it may not be dissolved, dispersed, or suspended, for example, in water or buffers, as described above.

In the above-mentioned embodiment (c), in order to form a complex substance of a "specific molecule in a sample" or a "specific molecule labeled by a labeling substance" and a "substance capable of changing dielectrophoretic properties of the specific molecule", a sample containing a "specific molecule" a "specific molecule labeled by a labeling substance" can be dissolved, dispersed, or suspended, respectively, for example, in water or buffers such as tris(hydroxymethylaminomethane) buffers, Good's buffers, phosphate buffers, borate buffers and the like to give liquid materials, and these liquid materials can be mixed and contacted with one another. The mixed liquid material can be mixed and contacted with a liquid material obtained by dissolving, dispersing, or suspending a "substance binding to the specific molecule" for example, in water or buffers such as tris(hydroxymethylaminomethane) buffers, Good's buffers, phosphate buffers, borate buffers or the like. Alternatively, those sample and substance may be disolved, dispersed or suspended at once.

If a sample containing a "specific molecule" is liquid, as described above, it may not be dissolved, dispersed, or suspended, for example, in water or buffers such as tris (hydroxymethylaminomethane) buffers and Good's buffers.

The complex containing liquid material thus obtained is then subjected to dielectrophoresis.

(General Equation of Dielectrophoretic Forces)

The equivalent dipole moment method is a procedure of analyzing dielectrophoretic forces by substituting induced charges for an equivalent electric dipole. According to this method, the dielectrophoretic force $F_d$ which a spherical particle with a radius of a is placed in an electric field E receives is given by:

$$F_d=2\pi a^3\epsilon_m Re[K^*(\omega)]\nabla(E_2) \quad (1)$$

wherein K*(ω) is expressed using the angular frequency of the applied voltage ω and the imaginary unit j as follows:

$$K^*(\omega)=\epsilon_p^*-\epsilon_m^*/\epsilon_p^*+2\epsilon_m^* \quad (2)$$

$$\epsilon_p^*=\epsilon_p-j\sigma_p/\omega,\epsilon_m^*=\epsilon_m-j\sigma_m/\omega \quad (3)$$

wherein $\epsilon_p$, $\epsilon_m$, $\sigma_p$, and $\sigma_m$ are permittivity and conductivity of the particle and the solution, and complex quantities are designated by *.

Equation (1) indicates that if Re[K*(ω)]>0, the force works such that the electric field attracts the particle toward a strong side (positive dielectrophoretic, positive DEP), and if Re[K*(ω)]<0, the force works such that the electric field pushes the particle toward a weak side (negative dielectrophoretic, negative DEP).

It can be understood from the above-mentioned general equation of dielectrophoretic forces that parameters involved in dielectrophoretic forces of substances receiving dielectrophoretic forces are, in general, permittivity and conductivity of the substances and the medium, the size of the substances, and the frequency of the applied electric field. These parameters should be set appropriately, depending on the type of separation improving substances to which a detecting complex substance has bound and labeling substances using for the detection of the specific molecule (molecule to be measured). Although it can not be mentioned in general, the permittivity of the medium employed is usually is not more than 13 mS/cm (as PBS concentration), and preferably not more than 1 mS/cm. For the size of the separation improving substances, in the case of particles, an average particle size is usually not more than 1 mm, and preferably 0.025 to 100 μm, and in the case of biological molecules, the size is usually more than 10 nm, and preferably more than 500 nm (estimated form sizes of normal protein molecules of a few to some tens nanometers).

(Electric Field Used for Dielectrophoretic Separation Employing Separation Improving Substances)

It can be said from the above-mentioned general equation of dielectrophoresis that parameters involved in dielectrophoretic forces of an applied electric field are the strength of the applied electric field and the applied frequency. In particular, even if substances are identical, since the applied frequency may cause changes in positive and negative dielectrophoretic properties, the parameters are to be set appropriately according to the specific molecule (molecule to be measured). These parameters should be set appropriately depending on the type of separation improving substances to which a detecting complex substance has bound and labeling substances using for the detection of the specific molecule (molecule to be measured). Although it can not be mentioned in general, if a separation improving substance of dielectrophoresis has a positive dielectrophoresis, the applied electric field strength is usually not more than 3.5 MV/m, and preferably not more than 1.0 MV/m. If a separation improving substance of dielectrophoresis has a negative dielectrophoresis, the electric field strength is not more than 3.5 MV/m. The applied frequency is usually in the region of 100 Hz to 10 MHz, and preferably 1 kHz to 10 MHz.

In the present invention, the electric field to be applied can be any of an AC electric field and a DC electric field, and it is generally preferable to use the AC electric field.

(Separation Method with Separation Improving Substances of Dielectrophoresis)

Separation methods of a specific molecule employing separation improving substances can be classified into two types as described below:

(Separation Method-1)

First, in the case where a separation improving substance is a substance which has the same positive or negative dielectrophoretic forces as molecules other than the specific molecule (molecule to be measured) [for example, a free labeling-substance (for example a specific substance labeled by a labeling substance which is not involved in a complex substance) employed for the detection of the specific molecule and the like] and is influenced by dielectrophoretic forces larger than the specific molecule (molecule to be measured), substantially, only the separation improving substance and the specific molecule bound to the separation improving substance are received large dielectrophoretic forces and separated.

That is, (1) for example, the specific molecule can be separated from the molecules other than the specific molecule by setting of the electric field strength and medium conditions in such a way that the separation improving substance and a molecule bound to the separation improving substance gather at a particular position on the dielectrophoresis electrode by dielectrophoretic forces, and the molecules other than the specific molecule (molecule not to be measured) [for example, a free labeling-substance employed for the detection of the specific molecule and the like] do not gather.

Additionally, (2) for example, separation can be carried out employing so-called dielectrophoretic chromatography apparatus (Field Flow Fractionation apparatus) in which separation is carried out with the interaction between the dielectrophoretic forces caused on the molecules from the electric field as described below and the molecular movement. In this case, since the separation improving substance and the molecule bound to the separation improving substance are only captured on the dielectrophoresis separation electrode by dielectrophoretic forces, or since differences take place between the moving speed of the separation improving substance and the molecule bound to the separation improving substance on one hand and that of the other molecules on the other hand the specific molecule can be readily separated from the molecules other than the specific molecule (molecules not to be measured).

(Separation Method-2)

Secondly, in the case where a separation improving substance is a substance which has different positive or negative dielectrophoretic forces from the molecules other than the specific molecule [for example, a labeling substance for use in detecting the specific molecule], that is, where a separation improving substance has positive dielectrophoretic forces and the molecules other than the specific molecule has negative dielectrophoretic forces, or otherwise a separation improving substance has negative dielectrophoretic forces and the molecules other than the specific molecule has positive dielectrophoretic forces, the separation improving substance and the specific molecule bound to the separation improving substance on one hand, and the molecules other than the specific molecule on the other hand move to different electric field regions respectively, and thus the specific molecule can be separated from the molecules other than the specific molecules.

That is, for example, (1) the separation improving substance and the molecule bound to the separation improving substance on one hand, and the molecules other than the specific molecule on the other hand move to substantially different electric field regions, respectively on the dielectrophoresis electrode by dielectrophoretic forces, so that the specific molecule can be separated from the molecules other than the specific molecule [for example, a labeling substance for use in detecting the specific molecule and the like].

Additionally, (2) separation can be performed, for example, using dielectrophoretic chromatography apparatus (Field Flow Fractionation apparatus). In this case, under conditions where the separation improving substance and the specific molecule bound to the separation improving substance have positive dielectrophoretic forces, and the molecules other than the specific molecule have negative dielectrophoretic forces, the separation improving substance and the specific molecule bound to the separation improving substance are captured on the dielectrophoretic separation electrode by dielectrophoretic forces, and the molecules other than the specific molecule are not captured on the electrode by negative dielectrophoretic forces. On the other hand, under conditions where the molecules other than the specific molecule have positive dielectrophoretic forces, and the separation improving substance and the specific molecule bound to the separation improving substance have negative dielectrophoretic forces, the molecules other than the specific molecule are captured on the dielectrophoretic separation electrode by dielectrophoretic forces, and the separation improving substance and the specific molecule bound to the separation improving substance are not captured on the electrode by negative dielectrophoretic forces. Thus, the specific molecule can be separated from the molecules other than the specific molecule.

For dielectrophoresis electrodes and dielectrophoretic chromatography apparatus which can be employed in the present invention, any ones which are usually employed in the art can be used. In particular, as discussed later, electrodes having a structure capable of forming a horizontally and vertically nonuniform electric field and apparatus equipped with the electrode as just above are included.

A "separation improving substance" is usually used in the form of being bound to a "substance binding to the specific molecule", whereby the substance can be bound to the "specific molecule" in a sample. Alternatively, direct binding of the "separation improving substance" to the "specific molecule" can be carried out by chemical binding methods such as methods for binding to the specific molecule through a functional group which is previously introduced into the surface of the separation improving substance, methods for binding the "specific molecule" to the separation improving substance via a linker, and the like. For the "substance specifically binding to the specific molecule" employed in this case can be used the same substance as the "substance specifically binding to the specific molecule" described previously [it is not required that it itself can be measured (detected) or labeled with a labeling substance by some method], or a substance possessing properties of binding specifically to a new site formed by forming a complex substance of the "specific molecule" and the "substance binding to the specific molecule", or the like. The substance possessing properties of binding specifically to a new site formed by forming a complex substance of the "specific molecule" and the "substance binding to the specific molecule" includes, for example, antibodies, peptide chains, nucleotide chains, and the like which can recognize the complex substance of the "specific molecule" and the "substance binding to the specific molecule and can bind to the complex substance".

Binding of the "separation improving substance" and the "substance binding to the specific molecule" can be carried out in a similar way as methods for labeling the "specific molecule" with a labeling substance as described above.

When a substance possessing properties of specifically binding directly to the "specific molecule" is used as a "separation improving substance", processes as described above are not required.

Such a "separation improving substance" includes, for example, nucleic acids, proteins, lipids, and the like.

In the present invention, "separating the complex substance from the molecules other than the 'specific molecule' contained in the sample" does not necessary mean to separate (isolate) only the "complex substance" (for example the complex substance of the specific molecule and the separation improving substance), but means to separate one or more kinds of substances other than the "complex substance" which co-exist in the sample and the "specific molecule" from each other depending on the purpose. In this case, if conditions are set as appropriate and the separation method according to the present invention is repeated, the "specific molecule" can be isolated as a complex substance thereof with the separation improving substance. In short, the object is to make it possible to measure an amount of the "specific molecule" or the "molecules other than the specific molecule" in a sample.

According to the separation method of the present invention as described above, the "specific molecule" (including cases of being collecting as a complex substance of the specific molecule and a separation improving substance) or the molecules other than the "specific molecule" can be collected.

Namely, in the case of (1) of Separation Method-1 described above, for example, the molecules other than the specific molecule" can be collected by washing the electrode with an appropriate buffer usually employed in the art, water, or the like while applying an electric field with such conditions that the specific molecule is captured as a complex substance with a separation improving substance at a particular position on the electrode and the other molecules are not captured at a particular position on the electrode, and then the specific molecule (a complex substance of the specific molecule and the separation improving substance) can be collected by ceasing from applying the electric field and washing the electrode with an appropriate buffer usually employed in the art, water, or the like.

In the case of (1) of Separation Method-2 described above, the separation improving substance and the molecule bound to the separation improving substance on one hand, and the molecules other than the specific molecule on the other hand move to substantially different electric field regions respectively on the dielectrophoresis electrode by dielectrophoretic forces, so that these moving molecules can be collected separately and respectively.

In the case where the separation is carried out by method (2) of Separation Method-1 described above, the specific molecule or the other molecules can be collected respectively by collecting at first a mobile phase which contains the molecules other than the specific molecule receiving small dielectrophoretic forces and moving without being captured at a particular position on the electrode, and after that, collecting a washed solution which contains the specific molecule by moving the specific molecule receiving large dielectrophoretic forces which is captured at a particular position on the electrode during applying the electric field by ceasing from applying the electric field and washing the electrode with an appropriate buffer usually employed in the art, water, or the like.

In the case where the separation is carried out by method (2) of Separation Method-2 described above, the specific molecule or the other molecule can be collected respectively, under conditions where the separation improving substance and the specific molecule bound to the separation improving substance have positive dielectrophoretic forces and the molecules other than the specific molecule have negative dielectrophoretic forces, by collecting at first a mobile phase which contains the molecules other than the specific molecule having negative dielectrophoretic forces and moving without being captured at a particular position on the electrode, and after that, collecting a washed solution which contains the specific molecule by moving the specific molecule having positive dielectrophoretic forces which is captured at a particular position on the electrode during applying the electric field by ceasing from applying the electric field and washing the electrode with an appropriate buffer usually employed in the art, water, or the like. Alternatively, the specific molecule or the other molecule can be collected respectively, under conditions where the molecules other than the specific molecule have positive dielectrophoretic forces and the separation improving substance and the specific molecule bound to the separation improving substance have negative dielectrophoretic forces, by collecting at first a mobile phase which contains the specific molecule having negative dielectrophoretic forces and moving without being captured at a particular position on the electrode, and after that, collecting a washed solution which contains the molecules other than the specific molecule by moving the molecules having positive dielectrophoretic forces and having been captured at a particular position on the electrode during applying the electric field by ceasing from applying the electric field and washing the electrode with an appropriate buffer usually employed in the art, water, or the like.

Buffers which can be employed include buffers which are usually employed in the art, for example, tris(hydroxymethylaminometane) buffers, Good's buffers, phosphate buffers, borate buffers, and the like.

A complex substance of the two members mentioned above (the "specific molecule" and the "substance capable of changing dielectrophoretic properties of the specific molecules") cannot be usually separated from the "substance capable of changing dielectrophoretic properties of the specific molecules" by dielectrophoresis. Further, a complex substance of the three members mentioned above (the "specific molecule" and the "substance binding to the specific molecule" and the "substance capable of changing dielectrophoretic properties of the specific molecules") cannot be usually separated from a complex substance of the "substance binding to the specific molecule" and the "substance capable of changing dielectrophoretic properties of the specific molecules" and the free "substance capable of changing dielectrophoretic properties of the specific molecules" by dielectrophoresis. Even if the separation are not achieved, however, there is no problem particularly in measuring the "specific molecules" in a sample as described later.

When a "substance capable of changing dielectrophoretic properties of the specific molecules" which binds to the "specific molecule" in a sample is used alone, not as a complex substance of the "substance capable of changing dielectrophoretic properties of the specific molecules" and a "substance binding to the specific molecule", since the "substance binding to the specific molecule" is used at an excess amount, the "substance binding to the specific molecule" is still remained. However thus retained substance binding to the specific molecule can be separated along with the molecules other than "the specific molecule".

A second embodiment of the present invention (a second method; hereinafter sometimes abbreviated as embodiment ②) relates to separating two or more kinds of molecules each other by placing a solution in which the two or more kinds of molecules are dissolved under a nonuniform electric field having an electric field strength of 500 KV/m or higher, the field being formed by an electrode having a structure capable of forming a nonuniform electric field.

The following describes this in detail.

According to the present invention, an electric field strength of 500 KV/m or higher allows to separate two or more kinds of molecules in a solution with one another which have not been separated in the past. A suitable electric field strength of the nonuniform electric field formed by the electrode as described above should be set appropriately, depending on the type of the two or more kinds of molecules in a solution, and although it can not be mentioned in general, it is selected appropriately in the range of 500 KV/m or higher, preferably 500 KV/m to 10 MV/m, more preferably 500 KV/m to 3.5 MV/m. Higher electric field strengths may cause difficulty in analysis due to generating heat. If such probabilities shall be expected, appropriate cooling of the electrode unit can be performed for example.

In the present invention, the electric field to be applied can be any of an AC electric field and a DC electric field, and it is generally preferable to use the AC electric field.

More specifically, for example, if a molecule to be measured is a nucleotide chain (oligonucleotide, polynucleotide), chromosome, and the like, the electric field strength is 500 KV/m or higher, preferably 500 KV/m to 10 MV/m, more preferably 500 KV/m to 3.5 MV/m. If a molecule to be measured is, for example, a peptide chain, a protein, and the like, the electric field strength is 500 KV/m or higher, preferably 1 MV/m to 10 MV/m, more preferably 1 MV/m to 3.5 MV/m.

The frequency of the nonuniform electric fields is usually 100 Hz to 10 MHz, and more preferably 1 kHz to 10 MHz.

In the case of embodiment ① of the present invention, since the separation is facilitated due to the use of a complex substance containing a"substance capable of changing dielectrophoretic properties of the specific molecule", two or more kinds of molecules can be separated respectively at a lower electric field strength than 500 KV/m. However, it is preferable to carry out the separation at 500 KV/m or higher, because the separation will become easier.

Two or more kinds of molecules in embodiment ② of the present invention include biological components such as nucleotide chains (oligonucleotide chains, polynucleotide chains), chromosomes, peptide chains (for example, C-peptide, angiotensin I, and the like), proteins (serum proteins such as immunoglobulin A (IgA), immunoglobulin E (IgE), immunoglobulin G (IgG), $\beta_2$-microglobulin, albumin, and ferritin; enzyme proteins such as amylase, alkaline phosphatase, and γ-glutamyltransferase; antiviral antibodies to viruses such as Rubella virus, Herpes virus, Hepatitis virus, ATL virus, and AIDS virus and antigenic substances from these viruses; antibodies to various allergens; lipids such as lipoproteins; and proteases such as trypsin, plasmin, serine proteases, and the like; sugar chains (for example, sugar chains of α-fetoprotein, CA19-9, prostate-specific antigen, carcinoembryonic antigen, substances having particular sugar chains produced by cancer cells); lectins (for example, concanavalin A, *Lens culinaris* lectin, *Phaseolus vulgaris* lectin, *Dutura stramonium* lectin, wheat germ lectin, and the like), and the like. In embodiment ② of the present invention, the two or more kinds of molecules are those which are soluble in a solution, and in embodiment ① of the present invention, the two or more kinds of molecules which are insoluble cause no problem.

According to embodiment ② of the present invention, among the above-mentioned molecules, if they are two or more kinds of molecules of the same type and having a different molecular weight, or two or more kinds of quite different molecules, the separation can be achieved. Combinations of two or more kinds of molecules of the same type and having a different molecular weight include, for example, combinations of molecules selected form nucleotide chains (oligonucleotides, polynucleotides) and chromosomes, and, for example, combinations of molecules selected form peptide chains, proteins, and the like. Combinations of two or more kinds of quite different molecules include, for example, combinations of molecule(s) selected from nucleotide chains (oligonucleotides, polynucleotides) and chromosomes with molecule(s) selected form peptide chains and proteins, combinations of sugars with molecule(s) selected form glucides, peptide chain and proteins and combinations of sugars with molecule(s) selected from peptide chains, proteins and lectins, and the like.

Solutions as described above in which the two or more kinds of molecules are dissolved include samples derived from a living body including body fluids such as serum, plasma, cerebrospinal fluid, synovial fluid and lymph, or excreta such as urine and feces, and treated materials thereof. Treated materials include, for example, appropriate dilutions of these samples derived from a living body with water, buffers, or the like, or those obtained from reconstitution by appropriately dissolving or suspending molecules as describes above from these body-derived samples in water, buffers, or the like. In the present invention, solutions in which two or more kinds of molecules are dissolved also include those containing molecules as described above, which are chemically synthesized.

Buffers which can be employed include buffers which are usually employed in the art, for example, tris(hydroxymethylaminometane) buffers, Good's buffers, phosphate buffers, borate buffers, and the like.

When a solution as described previously has a high conductivity, Joule heat generates by the current flowing in the solution as the voltage is applied, resulting in possibilities of boiling the solution. Therefore, it is preferable that the solutions are used with appropriate adjustment such that the conductivity is usually in the range of not more than 10 mS/cm, preferably not more than 200 μS/cm.

Figure 2:
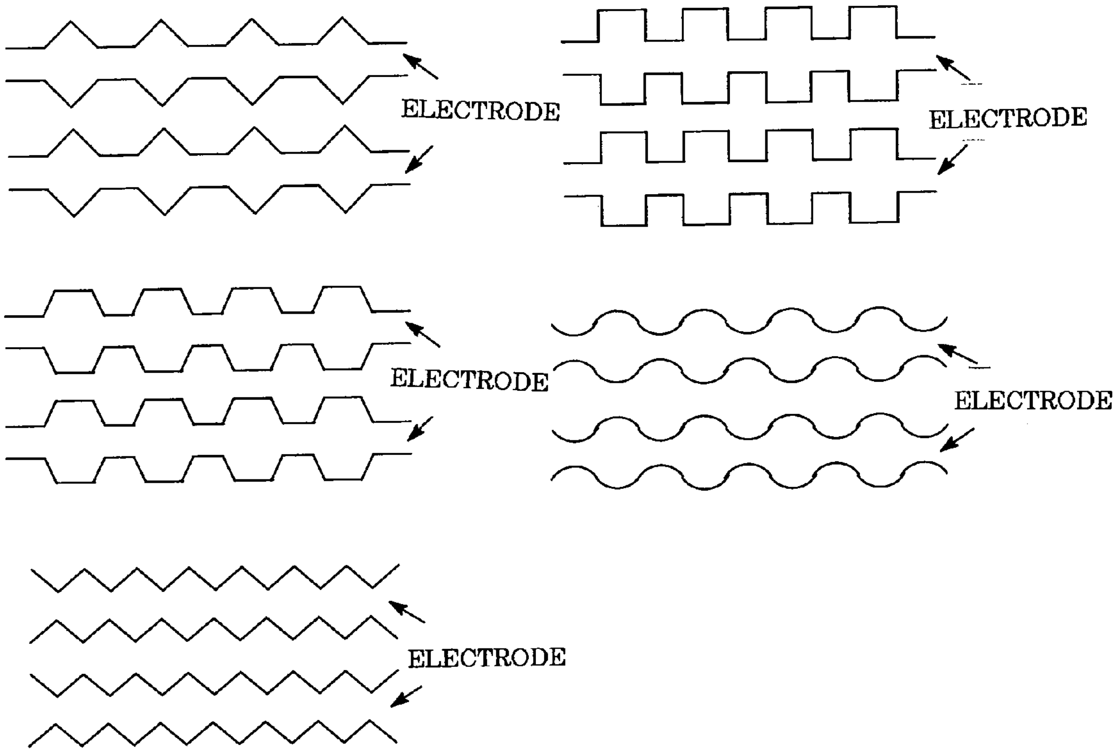
FIG. 2 is a representation showing specific examples of electrodes used in the present invention.

In the present invention, an electrode having a structure capable of forming a horizontally and vertically nonuniform electric field is one made of conductive materials such as, for example, aluminum, gold, and the like. Its structure can be any structure capable of causing dielectrophoretic forces, that is, forming a horizontally and vertically nonuniform electric field, including, for example, an interdigital shape [J. Phys. D: Appl. Phys. 258, 81–89 (1992); Biochim. Biophys. Acta., 964, 221–230 (1988), and the like]. More specifically, as shown in FIG. 2, shapes of triangle, square, trapezoid, sine-wave, or sawtooth, or the like are preferable, and structures with regularly and continuously repeating arrangements of these can be possible. When the electrode is used for the purpose of collecting a specific molecule, an electrode having a structure with such a regularly and continuously repeating arrangement is preferable.

Such an electrode is usually manufactured by placing an electrode having one or more pairs of the above-mentioned shapes in a comb-teeth manner on a substrate made of non-conductive materials such as, for example, glass, quartz, silicon, and the like employing micromachining technology known per se [Biochem. Biophys. Acta., 964, 221–230, and the like]. The distance between adjacent (facing) electrodes is not specified in particular, if a nonuniform electric field having a strong electric field strength can be formed, and although it can not be mentioned in general, should be appropriately set, depending on the type of molecules to be measured. For example, in the case of peptide chains, proteins, and the like, the distance between the widest portions in the electrode (minimum gap) is usually not more than 10 μm, preferably 5 μm, and in the case of nucleotide chains (polynucleotides, oligonucleotides) and the like, not more than 100 μm, preferably not more than 50 μm. In the case of chromosomes, the minimum gap is usually not more than 50 μm, preferably not more than 10 μm. It should be noted that if the distance between the adjacent (facing) electrodes is too large relative to the molecule of interest, it is impossible to form a nonuniform electric field having a sufficient electric field, and the distance is too small, it may be impossible to capture the molecule of interest.

The separation method according to embodiment ② of the present invention can be carried out, for example, in the following ways.

Method A

In order to separate two or more kinds of molecules dissolved in a solution each other by placing a solution in which the two or more kinds of molecules are dissolved under a nonuniform electric field formed with the electrode (electrode substrate) as described above, the separation can be performed according to differences in movement modes of molecules existing under a nonuniform electric field by setting such appropriate conditions that the nonuniform electric field is formed so as to move, only the molecule to be measured by dielectrophoretic forces (for example, only the molecule to be measured migrates to a particular position by dielectrophoretic forces and is captured at the particular position on the electrode, and the other molecules do not receive sufficient dielectrophoresis forces and are not captured at a particular position on the electrode). Alternatively, molecules can be separated at a weak position and a strong position in the electric field by setting such appropriate conditions that the molecule to be measured receives positive dielectrophoretic forces and the other molecules receive negative dielectrophoresis by adjusting the permittivity and conductivity of the medium and the frequency of the applied electric field.

Method B

The separation can be performed by allowing the molecule to be measured to move into the nonuniform electric field formed with the use of the electrode (electrode substrate) as described above and the then utilizing interaction caused therein between the dielectrophoretic forces caused to molecules by the electric field and the movement of the molecules. In this case, molecules receiving stronger dielectrophoretic forces move slower than those receiving weak dielectrophoretic forces, so that it is possible to make the separation of the molecules more easily.

Figure 3:
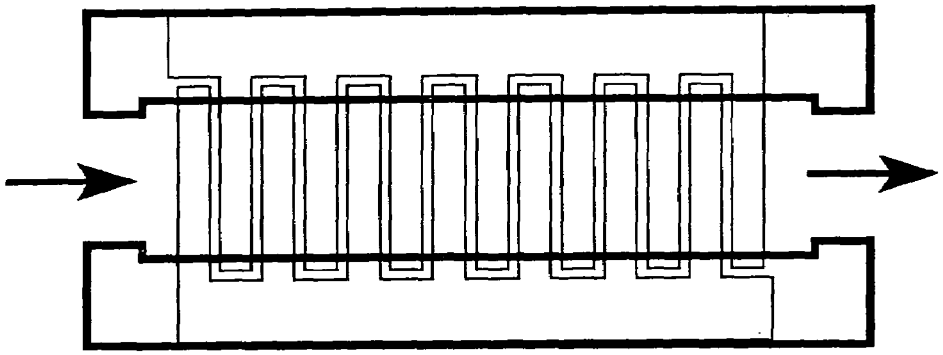
FIG. 3 is a representation showing one embodiment of electrode substrates having the flow path used in the present invention.

More specifically, an electrode substrate is employed which, as shown in FIG. 3, has the above-mentioned electrode and such a flow path that a solution in which the two or more kinds of molecules are dissolved can move on the electrode, and with applying a voltage to the electrode, a solution in which two or more kinds of molecules are dissolved can be allowed to move in a nonuniform electric field having an electric field strength of 500 kV/m or higher formed by the applied voltage. In FIG. 3, the arrow indicates the flow direction of a solution in which two or more kinds of molecules are dissolved.

Therefore, the molecules in a solution are attracted to the vicinity of an electrode having a stronger electric field by dielectrophoretic forces on the electrode. The movement of molecules is governed by three factors: the dielectrophoretic force $F_d$, the drag due to the flow in the flow path $F_v$, and the force due to the thermal movement $F_{th}$. ① in the case of $F_d >> F_v + F_{th}$, molecules are captured (trapped) on the electrode, ② in the case of $F_d << F_v + F_{th}$, molecules are eluted out with flow in the flow path, regardless of the electric field. ③ in the case of $F_d \approx F_v + F_{th}$, molecules are carried downwards with repeating adsorption and desorption on the electrode, so that the molecules arrive at the outlet with delay, relative to the set flow in the flow path. Therefore, if the separation is performed under conditions as in the above-mentioned case ①, it is possible to separate two or more kinds of molecules from each other, since the molecules receiving large dielectrophoretic forces are captured at a particular position on the electrode, and other molecules are not captured at a particular position on the electrode and flow out. If the separation is performed under conditions as in the above-mentioned case ③, it is possible to separate two or more kinds of molecules from each other, since the molecules receiving larger dielectrophoretic forces migrate at a slower speed in the flow path than molecules receiving smaller dielectrophoretic forces.

In Method B described above, a solution in which two or more kinds of molecules are dissolved can be moved, for example, by using physical medium flowing with a pump or the like, or electroosmotic flowing.

According to the separation method of embodiment ② of the present invention, it is possible to collect the specific molecule to be measured in a solution in which two or more kinds of molecules are dissolved.

Therefore, in the separation method, Method A, according to the present invention as described previously, the specific molecule or the other molecules can be collected respectively, for example, by separating the two or more kinds of molecules from each other in such a way that the specific molecule is captured at a particular position on the electrode and the other molecules are not captured at a particular position on the electrode, then washing the electrode with an appropriate buffer usually employed in the art, water, or the like while applying an electric field, and then ceasing from applying the electric field followed by washing the electrode with an appropriate buffer usually employed in the art, water, or the like.

In the separation method, Method B, according to the present invention as described previously, for example, when the separation is carried out under the above-described condition ①, the specific molecules or the other molecules can be collected respectively by collecting at first a mobile phase which contains molecules receiving small dielectrophoretic forces and moving without being captured at a particular position on the electrode, and after that, collecting a washed solution which contains molecules receiving large dielectrophoretic forces and having been captured at a particular position on the electrode during applying the electric field by allowing such molecules to move toward the flow path outlet by ceasing from applying the electric field and washing the electrode with an appropriate buffer usually employed in the art, water, or the like. When the separation is carried out under the above-described condition ③, the specific molecules or the other molecules can be collected respectively by collecting, at the flow path outlet, a mobile phase which contains molecules receiving small dielectrophoretic forces at first, and then a mobile phase which contains molecules moving at a slower speed and receiving larger dielectrophoretic forces.

The specific molecule to be measured in a solution can be measured by measuring any one of the two or more kinds of molecules separated by the separation method of embodiments ① and ② of the present invention by methods in accordance with properties of the molecule.

At first, the following description is given regarding to the cases where the separation method of embodiment ① of the present invention is employed.

A component (a specific molecule [a molecule to be measured] and/or the molecule other than the specific molecule) can be measured by separating a complex substance resulting from the interaction between the "specific molecule" (a molecule to be measured) and a "substance capable of changing dielectrophoretic properties of the specific molecule" which binds to the specific molecule from the molecules other than the specific molecule contained in the sample by the separation method of embodiment ① of the present invention, followed by measuring the specific molecule (the molecule to be measured) in the complex substance or the molecule other than the "specific molecule".

In the above-mentioned method, the "specific molecule" is one which can be measured (detected) itself or labeled with a labeling substance by some method, or alternatively one bound to a "substance binding to the specific molecule" which can be measured (detected) itself or labeled with a labeling substance. The labeling substance, the "substance binding to the specific molecule", and the labeling method are as described above.

In addition, a specific molecule (a molecule to be measured) in a sample can be measured rapidly and readily by carrying out the separation of a complex substance (complex substance 1) which is formed from the "specific molecule" (the molecule to be measured), the substance binding to the specific molecule and a "substance capable of changing dielectrophoretic properties of the specific molecule" which binds to the specific molecule from the (free) substance binding to the specific molecule which is not involved in the formation of the complex substance, so-called B/F separation, by the separation method of embodiment ① of the present invention, followed by measuring the complex substance 1, the specific molecule (the molecule to be measured) or the substance binding to the specific molecule in the complex substance 1, or the free substance binding to the specific molecule which is not involved in the formation of the complex substance.

In the above-mentioned methods, generally, as the substance binding to the specific molecule is used a "substance binding to the specific molecule" which can be measured (detected) itself or labeled with a labeling substance by some method.

Furthermore, by the separation method of embodiment ① of the present invention as described above is performed the separation of a complex of the specific molecule (the molecule to be measured), a substance binding to the specific molecule (or a molecule binding to the specific molecule labeled with a labeling substance), and a "substance capable of changing dielectrophoretic properties of the specific molecule" (a complex substance 1) formed by reacting the specific molecule (the molecule to be measured), a substance binding to the specific molecule (or a molecule binding to the specific molecule labeled with a labeling substance) and a "substance capable of changing dielectrophoretic properties of the specific molecule", from the free substance binding to the specific-molecule (or the free labeled substance binding to the specific-molecule). After that, it is possible to measure the presence or absence of the specific molecule (the molecule to be measured) in a sample by detecting the separated complex substance 1, based on the properties of the substance binding to the specific molecule in the complex substance 1 (or the labeling substance bound to the substance binding to the specific molecule within the complex substance 1).

Furthermore, it is possible to measure not only the presence of the specific molecule (the molecular to be measured) in a sample, but also to determine the amount of the specific molecule (molecular to be measured) in a sample quantitatively, for example, according to methods as described below.

By the separation method of embodiment ① of the present invention as described above is performed the separation of a complex substance of the specific molecule (the molecule to be measured), a substance binding to the specific molecule (or a labeled substance binding to the specific-molecule labeled with a labeling substance), and a "substance capable of changing dielectrophoretic properties of the specific molecule" (a complex substance 1), from the free substance binding to the specific-molecule (or the free labeled substance binding to the specific-molecule labeled with a labeling substance). After that, it is possible to measure the amount of the substance binding to the specific molecule in the complex substance 1 (or the amount of the labeling substance which is bound to the substance binding to the specific-molecule within the complex substance 1) or the amount of the free substance binding to the specific-molecule (or the amount of the labeling substance which is bound to the free substance binding to the specific-molecule) by measuring methods in accordance with the properties of the substance binding to the specific molecule or the labeling substance, and thus, the amount of the specific molecule (molecule to measured) in a sample, can be measured based on the amount.

Alternatively, the specific molecule in a sample can be measured by so-called competitive methods in which a labeled specific molecule is employed for competitive reactions between the labeled specific-molecule and the specific molecule in the sample.

Therefore, it is possible that by contacting a sample containing the specific molecule, the specific molecule labeled with a labeling substance (the labeled specific-molecule) and a "substance capable of changing dielectrophoretic properties of the specific molecule" with one another, a mixture of a labeled complex substance of the labeled specific-molecule and the "substance capable of changing dielectrophoretic properties of the specific molecule" and a complex substance of the specific molecule and the "substance capable of changing dielectrophoretic properties of the specific molecule" are formed and the mixture is subjected to dielectrophoresis to separate the complex substance containing the labeled specific-molecule from the free labeled specific molecule, and the amount of the labeling substance bound to the labeled specific-molecule in the separated labeled complex substance or the amount of the labeling substance bound to the free labeled specific-molecule is determined by measuring methods in accordance with the properties of the labeling substance, and the amount of a specific molecule in a sample is determined on the basis of the obtained amount.

In these above-mentioned methods, in order to determine the amount of the specific molecule in a sample on the basis of the resultant amount of the specific molecule, the substance binding to the specific molecule, or the labeling substance, the amount of the specific molecule in a sample can be calculated, for example, using respective calibration curves showing the relationship between the amounts of the specific molecule and the amounts of the labeling substance in the complex substance, the amount of the substance binding to the specific molecule in the complex substance (or the substance binding to the specific-molecule labeled by a labeling substance) the amounts of the labeling substance of the free labeled specific molecule, or the amount of the free substance binding to the specific-molecule (or the labeling substance in the labeled substance binding to the specific-molecule labeled by a labeling substance), the calibration curves being obtained by carrying out measurements in a similar way with samples having known concentrations of the specific molecule.

Further a relative amount of the specific molecule in a sample can be calculated and an error found among the dielectrophoretic separation devices can also be connected, for example, by adding to a sample a known concentration of a detectable substance as an internal standard, and by comparing an amount of the internal standard with an amount of the labeling substance or the substance binding to the specific molecule (or the labeled substance binding to the specific molecule) in a resulting complex substance, or an amount of the labeling substance in the free labeled specific molecule or the free substance binding to the specific molecule (or the labeling substance in the free labeled substance binding to the specific molecule).

In the above-mentioned method, the detectable substance is one which can be measured (detected) itself or labeled with a labeling substance by some method. For example, the detectable substance includes the concrete example as the specific molecule mentioned above and the separation improving substance, provided that it is one other than the component contained in the sample and it cannot bind to the molecule to be measured. The labeling substance, and the labeling method are the same as described above.

The following description is then given regarding to the cases where the separation method of embodiment ② of the present invention is employed.

The molecule to be measured (molecule A) in measuring methods employing the separation method of embodiment ② of the present invention can be any one which is the subject of the separation as described above and soluble in a solution as described above, wherein ① a molecule capable of interacting mutually with the molecule A to form a complex substance (a molecule B) exists, the molecule B possessing properties capable of being measured (detected) itself by some method or being able to be labeled with a labeling substance; or ② the molecule A can be labeled with a labeling substance and a molecule capable of interacting mutually with the molecule A to form a labeled complex substance (a molecule B) exists.

Therefore, the molecule A in a sample can be measured rapidly and readily by carrying out the separation of a complex substance resulting from the interaction between the molecule to be measured (the molecule A) and a substance specifically binding to the molecule to be measured (a molecule B) (complex substance 2), so-called B/F separation, by the separation method of embodiment ② of the present invention, and then measuring the complex substance 2, the molecule A or the molecule B in the complex substance 2 (or the labeling substance bound to the molecule B in the complex substance 2), or the free molecule B (or the labeling substance bound to the free molecule B).

Namely, a sample containing the molecule A is reacted with the molecule B (or the molecule B labeled with a labeling substance [a labeled molecule B]), and the resulting complex substance 2 of the molecule A and the molecule B (or the labeled molecule B), is separated from the free molecule B (or the labeled molecule B) by the separation method of embodiment ② of the present invention. After that, the presence or absence of the molecule A in the sample can be measured by detecting the separated complex substance 2, based on the properties of the molecule B in the complex substance 2 (or the labeling substance bound to the molecule B within the complex substance).

In addition, it is possible to measure not only the presence of the molecule A in a sample, but also to determine the amount of the molecule A in a sample quantitatively, for example, according to the following method.

That is, a sample containing the molecule A is reacted with, the molecule B (or the molecule B labeled with a labeling substance [a labeled molecule B]), and the resulting complex substance 2 of the molecule A and the molecule B (or labeled molecule B), is separated from the free molecule B (or the free labeled molecule B) by the separation method of embodiment ② of the present invention. After that, it is possible to measure the amount of the molecule B in the separated complex substance 2 (the labeling substance bound to the molecule B in the separated complex substance 2), or the amount of the free molecule B (or the labeling substance bound to the free labeled molecule B) by measuring methods in accordance with the properties of the molecule B or the labeling substance, and thus, the amount of the molecule A in the sample is measured on the basis of the obtained amount.

Alternatively, the molecule A in a sample can be measured by so-called competitive methods in which a labeled molecule A is employed for competitive reactions between the labeled molecule A and the molecule A in the sample.

Therefore, a sample containing a molecule A, the molecule A labeled with a labeling substance (the labeled molecule A), and a molecule B are reacted to form a labeled complex substance of the labeled molecule A and the molecule B and a complex substance of the molecule A and the molecule B, and then the labeled complex substance is separated from the free, labeled specific molecule to be measured A by the separation method according to the present invention as described above. After that, it is possible to measure the amount of the labeling substance bound to the labeled molecule A within the separated, labeled complex substance or the amount of the labeling substance bound to the free, labeled molecule A by measuring methods in accordance with the properties of the labeling substance, and thus the amount of the molecule A in the sample is measured on the basis of the obtained amount.

In these above-mentioned methods, in order to determine the amount of the molecule A in a sample on the basis of the resultant amounts of the molecule B or the labeling substance, the amount of the molecule A in a sample can be calculated, for example, using respective calibration curves showing the relationship between the amounts of the molecule A and the amounts of the labeling substance in the labeled complex substance, the amounts of the molecule B (or the labeling substance) in the complex substance the amounts of the labeling substance in the free, labeled molecule A, or the amounts of the free molecule B (or the labeling substance in the labeled molecule B), the calibration curve being obtained by carrying out measurements in a similar way with samples having known concentrations of the molecule A.

Further a relative amount of the specific molecule in a sample can be calculated and an error found among the dielectrophoretic separation devices can also be connected, for example, by adding to a sample a known concentration of a detectable substance as an internal standard, and by comparing an amount of the internal standard with an amount of the labeling substance or the molecule B (or the labeled substance binding to the specific molecule) in a resulting complex substance, or an amount of the labeling substance in the free labeled molecule A or the free molecule B (or the labeling substance in the free labeled molecule B).

In the above-mentioned method, the detectable substance is one which can be measured (detected) itself or labeled with a labeling substance by some method. For example, the detectable substance includes the concrete example as the specific molecule mentioned above and the separation improving substance, provided that it is one other than the component contained in the sample and it cannot bind to the molecule to be measured. The labeling substance, and the labeling method are the same as described above.

In the above-mentioned methods, the molecule specifically binding to the molecule A (a molecule B) is the same as the "substance specifically binding to the specific molecule" as described previously.

Labeling substances which can be used in the present invention are any substances usually used in such arts, as enzyme immunoassay (EIA), radioimmunoassay (RIA), fluoroimmunoassay (FIA), hybridization methods, and the like, and they are exemplified by enzymes such as alkaline phosphatase (ALP), β-galactosidase (β-Gal), peroxidase (POD), microperoxidase, glucose oxidase (GOD), glucose-6-phosphate dehydrogenase (G6PDH), malate dehydrogenase and luciferase; dyes such as Coomassie Brilliant Blue R250 and methyl orange; radioisotopes such as $^{99m}$Tc, $^{131}$I, $^{125}$I, $^{14}$C, $^{3}$H, $^{32}$P and $^{35}$S; fluorescent substances such as, for example, fluorescein, rhodamine, dansyl, fluorescamine, coumarin, naphthylamine or their derivatives and europium (Eu); luminescent substances such as luciferin, isoluminol, luminol and bis(2,4,6-trifluorophenyl) oxalate; substances having absorption in the ultra-violet region such as phenol, naphthol, anthracene, and their derivatives; substances having properties as spin labeling agents exemplified by compounds with oxyl groups such as 4-amino-2,2,6,6-tetramethylpiperidine-1-oxyl, 3-amino-2,2,5,5-tetramethylpyrroridine-1-oxyl and 2,6-di-t-butyl-α-(3,5-di-t-butyl-4-oxo-2,5-cyclohexadien-1-ylidene)-p-tolyloxyl, and the like.

Labeling of a molecule A or a molecule B with a labeling substance can be performed by any one of usual methods commonly used in such arts, as labeling methods commonly employing in EIA, RIA, FIA, hybridization methods, or the like, which are known per se [for example, Ikagaku Zikken Koza (Methods in Medical and Chemical Experiments) vol. 8, Edited by Y. Yamamura, 1st ed., Nakayama-Shoten, 1971; A. Kuwao, Illustrative Fluorescent Antibodies, 1st ed., Soft-science Inc., 1983; Enzyme Immunoassays, Edited by E. Ishikawa, T. Kawai, and K. Miyai, 3rd. ed., Igaku-Shoin, 1987; Molecular Cloning: A Laboratory Manual, 2nd. ed., J. Sambrook, E. F. Fritsch, and T. Maniatis, Cold Spring Harbor Laboratory Press, and the like], and usual methods employing reactions of avidin (or streptavidin) and biotin.

In the measuring method of the present invention (the second method, embodiment ②, conditions in reacting a molecule A and a molecule B (or a labeling molecule B) to form a complex substance 2, or reacting a molecule A, (or the labeled molecule A), and a molecule B to form a labeled complex substance can be such conditions that the formation of the complex substance 2 (or the labeled complex substance) is not inhibited. Therefore, such reactions can be carried out, for example, according to usual methods such as reaction conditions in forming the complex substance 2 (or the labeled complex substance) in EIA, RIA, FIA, hybridization methods, or the like which is known per se. Also, in the first method of the present invention, reaction conditions in forming a complex substance 1 of a specific molecule (the labeled specific-molecule), a substance binding to the specific molecule, and a "substance capable of changing dielectrophoretic properties" [or of a specific material (the labeled specific-molecule) and "substance capable of changing dielectrophoretic properties"] or a labeled complex substance of the labeled specific-molecule, a substance binding to the specific molecule, and a "substance capable of changing dielectrophoretic properties" can be those according to the above-mentioned reaction conditions.

In the method of embodiment ② of the present invention (the second method), the concentration of the molecule B (or labeled molecule B) used in reacting the molecule A and the molecule B (or the labeled molecule B) to form a complex substance 2 can not be mentioned in general due to varying according to the detection limit of the molecule A and the like, and it is preferable that the molecule B (or the labeled molecule B) is usually present in reaction solutions over a concentration allowing to bind to all of the molecules A corresponding to the given detection limit concentration, preferably over twice such a concentration, more preferably over five times higher such a concentration. Also, according to these conditions can be set the concentration of the "specific molecule" and the "substance binding to the specific molecule" (or the labeled "substance binding to the specific molecule"), or the "substance capable of changing dielectrophoretic properties of the specific molecule" to be used in the method of embodiment ① of the present invention (the first method).

In the method of embodiment ② of the present invention (the second method), the concentration of the labeled molecule A and the molecule B used in reacting the molecule A, the labeled molecule A, and the molecule B to form a labeled complex substance can be set as appropriate, depending on what level the detection limit of the molecule A and the measuring sensitivity, and the like are set at. The concentration of the labeled molecule A to be used is at least more than a concentration allowing to bind to all of the molecules B present in the reaction solution. Also, according to these conditions can be set the concentration of the "labeled specific molecules" and the "substance binding to the specific molecule" (or the labeled "substance binding to the specific molecule") used in the method of embodiment ① of the present invention (the first method).

In the method of embodiment ② of the present invention (the second method), the reaction pH and temperature, which can not be mentioned in general due to varying depending on the properties of the molecule A and the molecule B, can be in the range where the formation of the complex substance 2 (or the labeled complex substance) is not inhibited. The pH is usually in the range of 2 to 10, preferably 5 to 9, and the temperature is usually in the range of 0 to 90° C., preferably 20 to 80° C. For the reaction time, the time required for forming a complex substance 2 (or the labeled complex substance) is different depending on the properties the molecule A and the molecule B, and the reaction can be usually performed as appropriate for a period of a few seconds to a few hours. Also, the reaction pH, temperature, and reaction time in the method of embodiment ① of the present invention (the first method) can be adjusted according to these conditions.

In the measuring methods of the present invention, measurements can be carried out by respective predetermined methods according to the type of the analytes, in order to measure the molecule B in the separated complex substance 2 (or the labeling substance bound to the molecule B in the complex substance 2), the free molecule B (or the labeling substance bound to the free, labeled molecule B), the substance binding to the specific molecule in the complex substance 1 (or the labeling substance bound to the substance binding to the specific molecule in the complex substance 1), the free substance binding to the specific-molecule (or the free substance binding to the specific-molecule labeled by a labeling substance), the labeling substance bound to the labeled molecule A in the labeled complex substance, the labeling substance bound to the labeled molecule A, the labeling substance bound to the labeled specific-molecule in the labeled complex substance, or the labeling substance bound to the free, labeled specific-molecule. For example, if they have enzyme activities, measurements can be carried out according to usual methods such as EIA and hybridization methods, for example, methods described in Enzyme Immunoassays (Proteins, Nucleic acids, and Enzymes, Extra issue No. 31), Edited by T. Kitagawa, T. Nambara, A. Tsuzi, and E. Ishikawa, pp. 51–63, Kyoritsu Publishing Inc., Published on Sep. 10, 1987) and the like. If substances to be measured are radioactive, measurements can be carried out by selecting an appropriate measurement instrument such as an immersion GM counter, liquid scintillation counter, well-type scintillation counter, or the like, depending on the type and the strength of radiation emitted from the radioactive substances, according to usual methods such as RIA and hybridization methods (see, for example, Methods in Medical and Chemical Experiments, vol. 8, Edited by Y. Yamamura, 1st ed., Nakayama-Shoten, 1971; Methods in Biochemical Experiments 2: Tracer Experiments Part II, S. Takemura and T. Honzyo, pp. 501–525, Tokyo Kagaku Dozin, Inc., Published on Feb. 25, 1977). If their properties are fluorescent, measurement can be carried out according to usual methods such FIA and hybridization methods employing measurement instruments such as fluorophotometers, confocal laser microscopes, or the like, for example, methods described in Illustrative Fluorescent Antibodies (A. Kuwao, 1st ed., Softscience Inc., 1983), Methods in Biochemical Experiments 2: Chemistry of Nucleic Acids III, M. Miyoshi, pp. 299–318, Tokyo Kagaku Dozin, Inc., Published on Dec. 15, 1977), and the like. If their properties are luminescent, measurement can be carried out according to usual methods employing measurement instruments such as photon counters, for example, methods described in Enzyme Immunoassays (Proteins, Nucleic acids, and Enzymes, Extra issue No. 31), Edited by T. Kitagawa, T. Nambara, A. Tsuzi, and E. Ishikawa, pp. 252–263, Kyoritsu Publishing Inc., Published on Sep. 10, 1987) and the like. If their properties are those possessing absorption in the ultra-violet region, measurement can be carried out by usual methods employing measurement instruments such as spectrophotometers, and if their properties are chromogenic, measurement can be carried out by usual methods employing measurement instruments such as spectrophotometers and microscopes. If their properties are spin properties, measurement can be carried out according to methods employing electron spin resonance instruments, for example, methods described in Enzyme Immunoassays (Proteins, Nucleic acids, and Enzymes, Extra issue No. 31), Edited by T. Kitagawa, T. Nambara, A. Tsuzi, and E. Ishikawa, pp. 264–271, Kyoritsu Publishing Inc., Published on Sep. 10, 1987) and the like.

In the measurement methods of the present invention, for measuring respective molecules separated by the separation methods according to the present invention as described above, measurements can be carried out, for example, by measuring whether or not the complex molecule or the complex substance and/or the free molecule B or the free "substance binding to the specific molecule" are separated or captured at a particular position on the electrode (a strong and/or a weak electric field region), by direct observation of the molecule B in the complex substance 2 (or the labeling substance bound to the molecule B in the complex substance 2), the free molecule B (or the labeling substance bound to the free, labeled molecule B), the substance binding to the specific molecule in the complex substance 1 (or the labeling substance bound to the substance binding to the specific molecule in the complex substance 1), or the free substance binding to the specific-molecule (or the free labeled substance binding to the specific-molecule). In this case, it is preferable that the molecule B, specific molecule, or labeling substance has properties of radioactivity, fluorescence, luminescence, chromogen, spin, or the like.

An eluting solution from the electrode substrate as described above can be guided directly to a detection unit, wherein the molecule B in the complex substance 2 (or the labeling substance bound to the molecule B in the complex substance 2) in the eluting solution, the free molecule B (or the labeling substance bound to the free, labeled molecule B) in the eluting solution, the substance binding to the specific molecule in the complex substance 1 (or the labeling substance bound to the substance binding to the specific molecule in the complex substance 1) in the eluting solution, the free substance binding to the specific-molecule (or the free labeled substance binding to the specific-molecule) in the eluting solution, the labeling substance bound to the labeled molecule A in the labeled complex substance in the eluting solution, the labeling substance bound to the free, labeled molecule A in the eluting solution, the labeling substance bound to the labeled specific-molecule in the labeled complex substance in the eluting solution, or the labeling substance bound to the free, labeled specific-molecule in the eluting solution can be measured directly. Alternatively, a similar measurement to the above can be conducted with the use of the electrode equipped with the detection unit. By using such methods as above, measurements can be conducted more rapidly.

In this case, if enzyme activities are the properties which are detectable by some method and possessed by molecule B, the substance binding to the specific molecule, the specific molecule or the labeling substance, it is necessary to provide a reaction unit between the downstream terminal of the electrode on the substrate and the detection unit, to which reagents for measuring the enzyme activities are supplied to carry out the reaction with the eluting solution. The reagents for measuring the enzyme activities used in the reaction unit may be those which are prepared according to the methods described in Enzyme Immunoassays (Proteins, Nucleic acids, and Enzymes, Extra issue No. 31), Edited by T. Kitagawa, T. Nambara, A. Tsuzi, and E. Ishikawa, pp. 51–63, Kyoritsu Publishing Inc., Published on Sep. 10, 1987) and the like, or employed reagents of commercial available kits for clinical test may be selected appropriately for this use. Also in the case where the properties of the molecule B or the labeling substance are not enzyme activities, it is optional to provide an suitable reaction unit between the downstream terminal of the electrode on the substrate and the detection unit, to which predetermined reagents are supplied to react for the purpose of increasing the detection sensitivity and the like.

Among the two measurement methods, in the latter method, that is, the method in which respective molecules are guided to the detection unit after the separation on the electrode, it is likely that the efficiency of separation is reduced, or the detection sensitivity of the molecules which have been separated is reduced, due to influences by, for example, the flow rate of the eluting solution, the shape of the elution flow path, the diffusion into the eluting solution of each molecule during moving to the detection unit, and the like. Therefore, if only a specific molecule is intended to be detected, the former method, that is, the method in which the separated respective molecules are detected by observing directly the surface of the electrode after the separation on the electrode is advantageous, for example, because this method can overcome various problems resulting from influences by the diffusion, for instance as described above, and additionally the time required from separation to detection can be reduced by this method since there is no need for guiding the separated respective molecules to the detection unit. Also, this method is advantageous, for example, in that the method leads to reducing the space of the substrate since the reaction, separation, and detection are carried out on the electrode substrate, and thus the reaction, separation, and detection units can be integrated, and furthermore a detecting device itself can be expected to be miniaturized, since the feeding of a eluting solution is not required.

The measurement methods of the present invention can be carried out according to known methods per se as described above, except for employing the separation methods of the present invention, and used reagents are also selected as appropriate according to methods known per se.

It is advantageous to carrying out the above-mentioned methods of the present invention to prepare, in advance, a dielectrophoretic measurement kit comprising reagents and the others for use in carrying out the present invention.

Specifically, the dielectrophoretic measurement kit of the present invention comprises a "substance binding to the specific molecule" and a "substance capable of changing dielectrophoretic properties of the specific molecule", wherein these substances can form a complex substance with the "specific molecule" in a sample.

Alternatively, the dielectrophoretic measurement kit of the present invention comprises the "specific molecule labeled with a labeling substance", a "substance binding to the specific molecule", and a "substance capable of changing dielectrophoretic properties of the specific molecule", wherein these substance can form a complex substance with the "specific molecule" in a sample or the "specific molecule labeled with a labeling substance".

In the above-mentioned kits, preferable embodiments and specific examples of the "substance binding to the specific molecule", the "substance capable of changing dielectrophoretic properties of the specific molecule", and "specific molecule labeled with a labeling substance" are as described above, and the "substance capable of changing dielectrophoretic properties of the specific molecule" is preferably a substance binding to either or both of the "specific molecule" and the "substance binding to the specific molecule". The above-mentioned kits can further be combined with a dielectrophoretic apparatus.

In addition, the kits can also contain reagents usually used in the art as described above, standards of the specific molecule or the molecule A, and the like.

The following will describes the measurement methods of the present invention in more detail, giving an example in the case of employing a hybridization method for detecting a specific gene sequence.

At first, a nucleotide probe having an appropriate length which has a sequence complementary to the gene sequence to be detected (or measured) and has been labeled with a labeling substance, and unknown genes which are denatured to the single strand are mixed and reacted in a suitable buffer, and annealed to form a complex of the nucleotide probe and the unknown genes denatured to the single strand. Then, the resulting reaction solution is subjected to the separation method of the present invention employing dielectrophoretic forces as described above to separate the complex from the free nucleotide probe. After separation, the labeling substance in the complex is measured by the methods as described above, so that it is possible to detect or measure whether the unknown genes contain the sequence complementary to the nucleotide probe, that is, the presence or absence of the sequence complementary to the nucleotide probe.

In the above-mentioned methods, the nucleotide probe and buffers can be selected appropriately according to methods known per se. Method for preparing a nucleotide probe and unknown genes denatured to the single strand, annealing conditions, and the like can be performed according to methods known per se.

The present invention will be further described in detail with reference to Examples, Reference Examples, and Experimental Examples, which do not intend to limit the present invention in any way.

EXAMPLES

Reference Example 1

Manufacture of Dielectrophoretic Electrode Substrate

A multi-electrode array having a minimum gap of 7 μm, an electrode pitch of 20 μm, and the number of electrodes of 2016 (1008 pairs) was designed, and a photomask according to the design was made for manufacturing the electrode as follows.

On a glass substrate on which aluminum was deposited and to which a photoresist was applied, an electrode pattern as designed was drawn on an electron beam drawing machine, and then the photoresist was developed and the aluminum was etched to make the photomask.

The electrode substrate was manufactured according to the method described in T. Hashimoto, "Illustrative Photofabrication", Sogo-denshi Publication (1985), as follows.

The photomask thus made was contacted tightly with the aluminum-deposited glass substrate to which a photoresist was applied, and then exposed to the electrode pattern with a mercury lamp. The electrode substrate was manufactured by developing the exposed glass substrate for the electrode and etching the aluminum surface, followed by removing the photoresist remained on the aluminum surface. The aluminum surface, which had electrochemical activities, was provided with an organic thin coating having a thickness of 5 nm by spin-coating a diluted photoresist.

Figure 4:
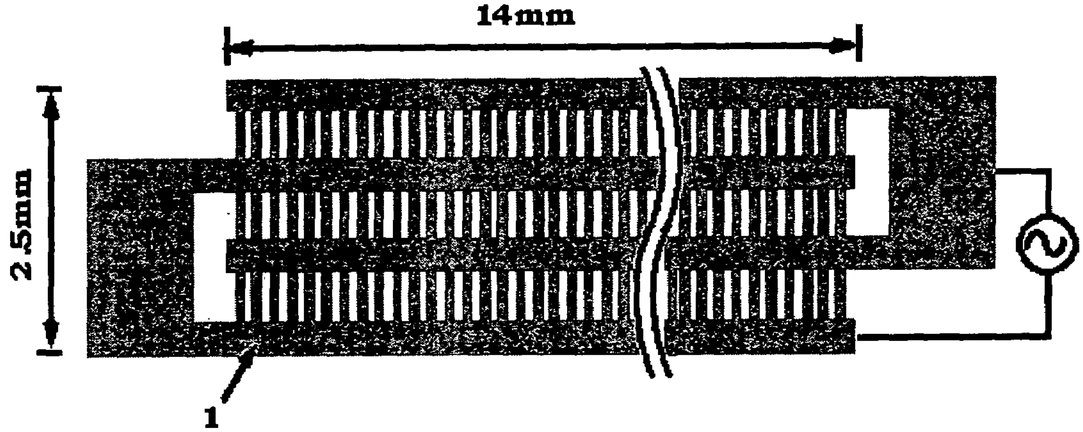
FIG. 4 is a schematic view of the dielectrophoresis electrode substrate manufactured in Reference Example 1.
Figure 5:
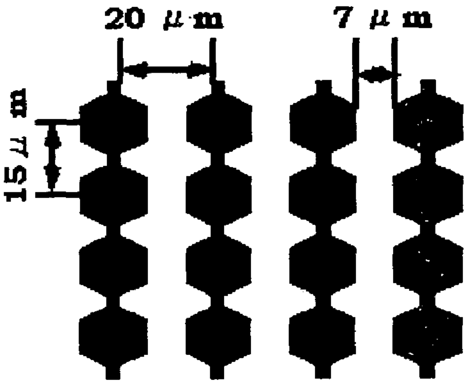
FIG. 5 is a schematic view of the electrode manufactured in Reference Example 1.

FIGS. 4 and 5 show the schematic views of the manufactured electrode substrate and the electrode, respectively. In FIG. 4, 1 indicates the electrode.

Reference Example 2

Manufacturing an Electrode Substrate Having a Flow Path

In order to separate molecules by the movement of the molecules under an nonuniform AC electric field, a flow path on the electrode substrate manufactured in Reference Example 1 was made using silicone rubber.

The silicone-rubber flow path for sending a molecule dissolving solution on the electrode had a depth of 25 μm and a width of 400 μm and was designed such that the flow path runs through a region in which the electrode on the electrode substrate was placed.

Its manufacturing was carried out according to the method described in T. Hashimoto, "Illustrative Photofabrication", Sogo-denshi Publication (1985). At first, a sheet-type negative photoresist having a thickness of 25 μm was applied onto the glass substrate, exposed with a photomask designed for making the flow path, and the negative photoresist was developed. Uncured silicone rubber was cast using the negative-photoresist substrate as a template, and then was cured to produce a silicon rubber surface having the concave surface with a height of 25 μm in the region where the electrode was placed.

The electrode substrate and the silicone-rubber flow path were adhered with a two-fluid-type curing silicone rubber such that the concave surface of the silicone rubber was faced to the region where the electrode on the electric substrate was placed. A syringe for injecting a solution was placed upstream of the flow path, and an apparatus allowing a solution in which the molecules were dissolved to flow on the electrode was added to the electrode substrate.

Figure 6:
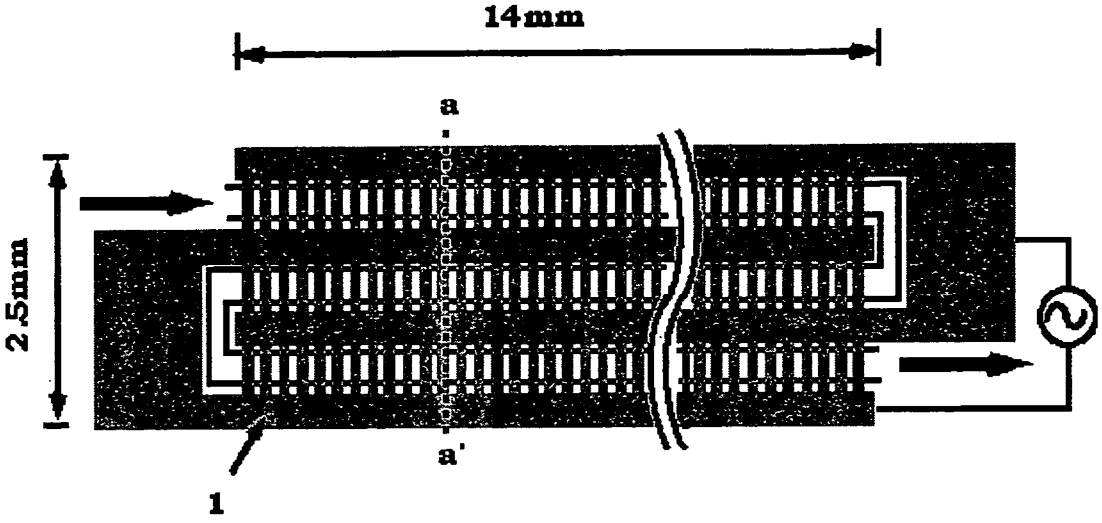
FIG. 6 is a schematic view of the electrode substrate having the flow path manufactured in Reference Example 2.
Figure 7:
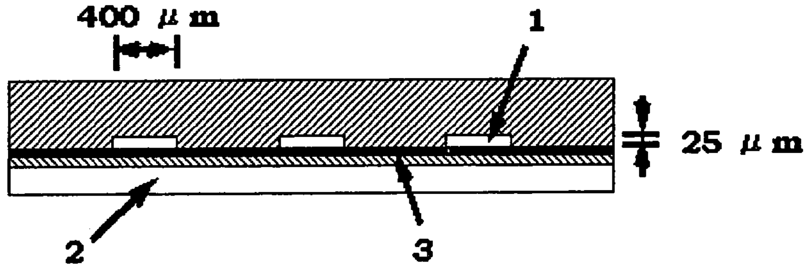
FIG. 7 is a schematic view of the section along the line a–a' of FIG. 6.

FIGS. 6 and 7 show the schematic views of the electrode substrate having the formed flow path and the section along the line a–a', respectively. In FIG. 6, 1 indicates the electrode, and the arrow represents the direction of the movement of a solution in which two or more kinds of molecules are dissolved.

Example 1

Detection of Biotin Molecules with a Dielectrophoretic Chromatography Apparatus (Field-Flow Fractionation Apparatus)

Biotin was bound to λDNA as a separation improving substance of dielectrophoresis to give biotinylated λDNA, which was then mixed with a fluorescein-labeled anti-biotin antibody to carry out the antigen-antibody reaction with the use of the resultant as a sample, quantitative detection of biotin molecules was carried out with a dielectrophoretic chromatography apparatus.

(Reagents)

The biotinylated λDNA in which biotin was coupled with λDNA was prepared using Photo-Biotin Labeling Kit (Nippon Gene Co. Ltd.) according to the appended preparing protocol. The components were then mixed at ratios as shown in Table 1 in 50 mM PBS (pH 7.5) to carry out the antigen-antibody reaction. The concentration of total λDNA in each sample was adjusted to 0.32 nM by adding non-biotinylated λDNA, which is equal to the concentration of the biotinylated λDNA in the sample having a biotin concentration of 128 nM (Sample No. 5).

TABLE 1

| Sample No. | Concentration Biotin | Fluorescein-labeled anti-biotin antibody |
|---|---|---|
| 1 | 0 nM | 5.7 nM |
| 2 | 0.8 nM | 5.7 nM |
| 3 | 1.6 nM | 5.7 nM |
| 4 | 3.2 nM | 5.7 nM |
| 5 | 128 nM | 5.7 nM |

After the antigen-antibody reaction was completed, the medium of the reactions was substituted by 2.5 mM carbonate buffer (pH 10) to make samples, using an ultrafiltration filter having a cut-off molecular weight of 50000.

(Procedures)

The reaction solutions described above were fed to the electrode substrate having the flow path formed in Reference Example 2 at a flow rate of 800 μm/sec at the sample injection port using a microsyringe pump (KSD 100, Aishisu Co., Inc.). The applied electric field had a frequency of 1 MHz and an electric field strength of 0.9 MV/m (defined as the applied voltage/7 μm of the minimum gap).

The above-mentioned molecule samples were introduced into the sample injection port on the electrode substrate, and the amount of fluorescence was measured near the outlet of the flow path with applying the predetermined electric field for a period of 30 to 80 seconds after introducing each sample.

Measurements were carried out by taking fluorescent images every about five seconds at a flow path area near the outlet of the flow path under a confocal laser microscope (LSM-GB 200, Olympus Optical Co., Ltd.) and calculating the sum of brightness values of all the pixels (hereinafter referred to the fluorescence amount). In the measurements, when perfect confocal images are used, in the case where the distribution of fluorescent intensity takes place with the depth of the flow path, accurate results are not obtained. Thus, the orifice on the photomultiplier of the laser microscope was opened fully so as to permit to integrate and measure the fluorescence depending on the depth as well.

The capture ratio can be calculated from the following equation 1.

In these measurements, when the electric field is not applied, the fluorescence amount measured at the electrode outlet is equal to that at the inlet, since samples having fluorescence-labeled molecules move on the electrode structure by means of the syringe pump. However, when the electric field is applied and molecules are attracted to the electrode by dielectrophoresis forces, the fluorescence amount will be decreased. Therefore, the decreased amount in the fluorescence amount is taken as the captured amount of molecules and used to indicate the amount of molecules attracted to the electrode when the total amount of the initial molecules is consider to be 100.

$$\text{Capture Ratio}(\%)=(F_{-}-F_{+})\times 100/F \quad (1$$

wherein, $F_{-}$: the fluorescence amount without applying the electric field $F_{+}$: the fluorescence amount during applying the electric field (Results)

Figure 8:
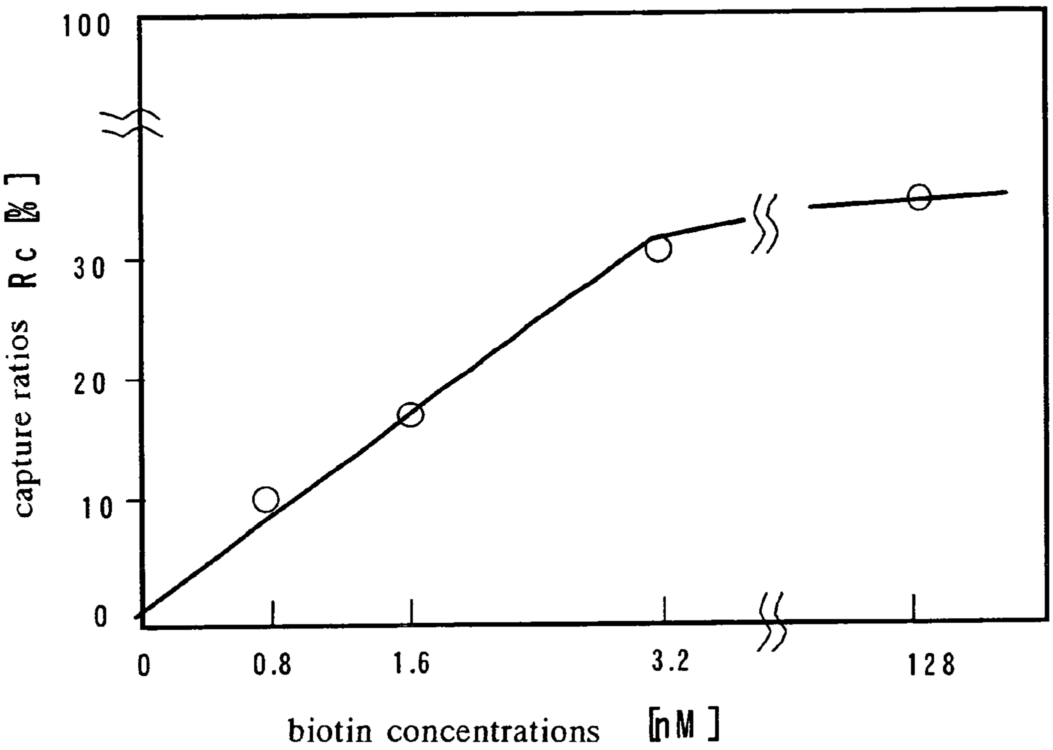
FIG. 8 is a graph showing the relationship between biotin concentrations and capture ratios obtained in Example 1.

The results are shown in FIG. 8. At 0.9 MV/m of the electric field strength employed in these experiments, the capture ratio was about 100% for the λDNA and 0% for the fluorescein-labeled anti-biotin antibody. At a biotin concentration of 0 pM, since there was no biotinylated λDNA which was recognized by the fluorescein-labeled anti-biotin antibody, the labeled antibody was not trapped on the electrode, and the capture ratio displayed almost 0%. It is expected that when the biotinylated λDNA is added, the labeled antibody forming a complex with the biotinylated λDNA trapped on the electrode is also trapped on the electrode, since the fluorescein-labeled anti-biotin antibody is bound to biotin by the antigen-antibody reaction. Therefore, the capture ratio indicated in this case is to represent the ratio of the antibody bond to the biotinylated λDNA among the total labeled anti-biotin antibody which is contained in the sample. In biotin concentrations of 0 to 3.2 nM, the capture ratio was increased proportionally to increasing the biotin concentration, and thus it can be said that the antigen is detected quantitatively. In contrast, for samples having the biotin concentration added at 3.2 nM or higher, little increase in the capture ratio was found and the capture was on the order of almost 30%. As this cause, it may be likely that the fluorescein-labeled anti-biotin antibody used in this Example had a low antibody titer, and the antibody capable of binding to biotin was present on the order of only 30% of the total antibody.

Until now, it is impossible to separate a complex of biotin and a fluorescein-labeled anti-biotin antibody from an unreacted fluorescein-labeled anti-biotin antibody by dielectrophoretic chromatography and the detection of a complex with biotin has not been achieved, because there is no difference in dielectrophoresis separation between the complex and the unreacted antibody to a sufficient extent. The above-mentioned results indicate that applications of a separation improving substance can permit to detect quantitatively by dielectrophoretic chromatography, molecules which have not been detected until now.

Example 2

Detection of α-Fetoprotein (AFP) with Antibody-Immobilized Latex Beads as a Separation Improving Substance Alpha-fetoprotein (AFP) was reacted with latex beads on which an anti-α-fetoprotein (AFP) antibody A4-4 was immobilized, and a complex was formed by further reacting with a fluorescein-labeled anti-AFP antibody WA1 Fab' having a different epitope from that of A4-4. AFP was detected by separating the complex from the uncomplexed fluorescein-labeled anti-AFP antibody WA1 on the electrode.

2-1 Detection of AFP in Buffer (Reagents)

Preparation of anti-AFP antibody immobilized latex beads:

1.2 mg of an anti-AFP antibody A4-4 prepared by the inventors and 10 mg of latex beads with a diameter of 120 nm (reagent latex N-100, Sekisui Chemical Co., Inc.) were mixed in a citrate solution (pH 3), and then the beads were collected as precipitates by centrifugation. The collected beads were suspended in 2.5% BSA solution to block the surface of the beads, yielding latex beads on which the anti-AFP antibody A4-4 was adsorbed. The prepared latex beads had adsorbed 123 μg anti-AFP antibody A4-4 per 1 mg of the latex beads.

Preparation of fluorescein-labeled anti-AFP antibody WA1 Fab':

40 mg of an anti-AFP antibody WA1 was digested with pepsin, and then reduced with 2-aminoethanethiol (Wako Pure Chemicals Industries, Ltd.) to prepare 15 mg of the Fab'. 15 mg of the anti-AFP antibody WA1 Fab' and 150 μg of fluorescein isothiocyanate (Wako Pure Chemicals Industries, Ltd.) were mixed in 10 ml carbonate buffer solution (pH 9), and a fluorescein-labeled anti-AFP antibody WA1 Fab' was prepared using a NAP-25 column (Amersham pharmacia biotech).

Reaction:

The antigen-antibody reaction was carried out by mixing the components as shown in Table 2 in 50 mM PBS (pH 7.5) and allowing standing at room temperature for 2 hours.

TABLE 2

| Sample No. | Anti-AFP antibody A4-4 immobilized latex | AFP | Fluorescein-labeled anti-AFP WA1 Fab' antibody |
|---|---|---|---|
| 1 | 0.10% | 0 μM | 0.70 μM |
| 2 | 0.10% | 0.09 μM | 0.70 μM |
| 3 | 0.10% | 0.18 μM | 0.70 μM |
| 4 | 0.10% | 0.35 μM | 0.70 μM |

After the antigen-antibody reaction was completed, the reaction solutions were diluted 100 times with distilled water, and the resultants were subject to the dielectrophoretic separation.

(Procedures)

Onto the dielectrophoretic electrode described in Reference Example 1 was dropped 20 μl of the above-mentioned solutions, and a cover glass having each side of 22 mm was placed. Fluorescent images before and during applying the electric field were taken using a confocal laser microscope. The applied electric field had a frequency of 100 kHz and an electric field strength of 1.4 MV/m.

Analysis of fluorescent images was performed using an image analysis software Scion Image. After the color tone gradation of fluorescent images before and during applying the electric field was averaged, the gradation of color tone of images before applying the electric field was subtracted from that during applying the electric field, such that only areas having fluorescence increased by applying the electric field were indicated. The densitogram of the areas having an increase in fluorescence was obtained to express the increased amount of fluorescence as image output concentration values.

(Results)

As the results of dielectrophoresis on the electrode, the beads moved to a weak region in the electric field strength due to receiving negative dielectrophoretic forces, and the other biological molecules including the unreacted fluorescein-labeled anti-AFP antibody WA1 Fab' moved to a strong region in the electric field strength due to receiving positive dielectrophoretic forces, and thereby allowing separating, on the electrode, the anti-AFP antibody immobilized latex beads/AFP/fluorescein-labeled anti-AFP antibody WA1 Fab' complex from the unreacted fluorescein-labeled anti-AFP antibody WA1 Fab'.

Figure 9:
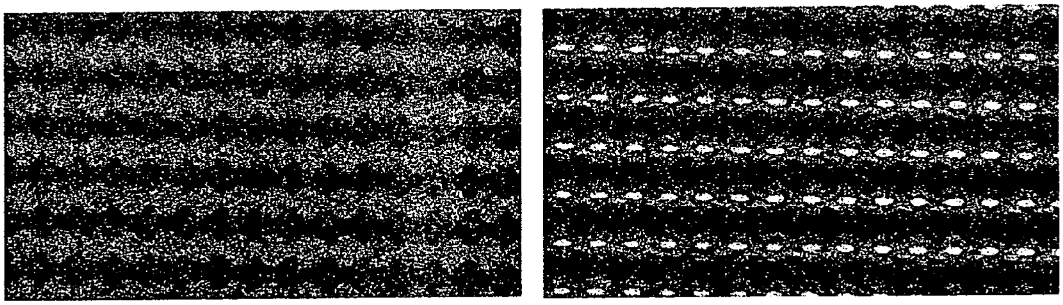
FIG. 9 is fluorescent images on the electrode obtained in Example 2, taken by a laser microscope before and during applying an electric field.
Figure 10:
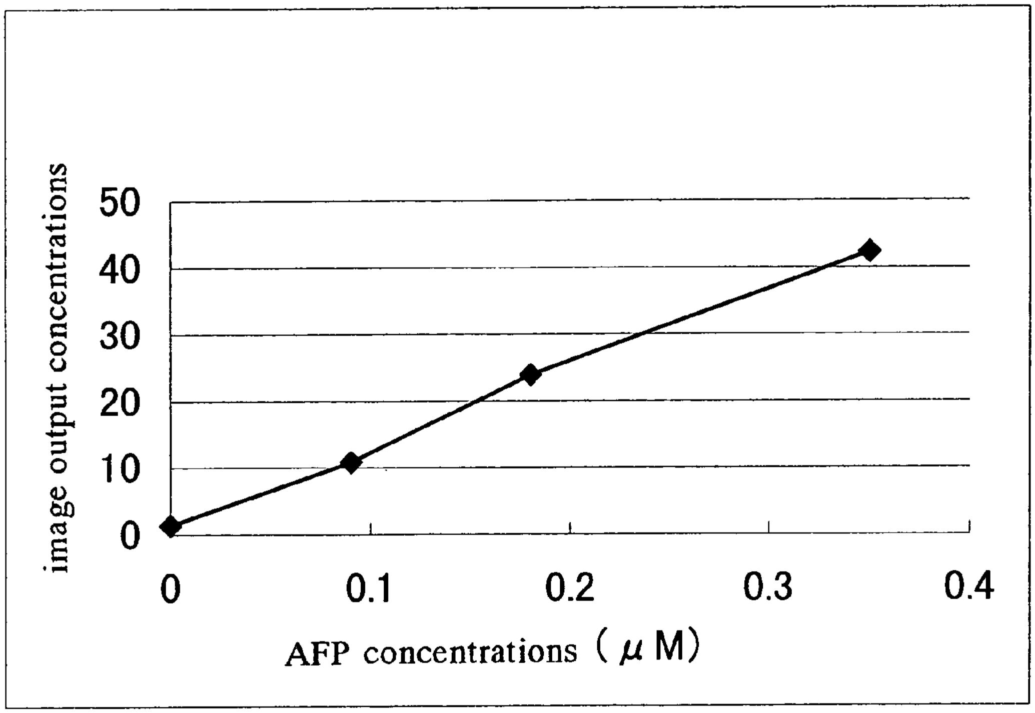
FIG. 10 is a graph showing the relationship between AFP concentrations and image output concentrations obtained in Example 2.

FIG. 9 shows fluorescent images on the electrode taken from the laser microscope before and during applying the electric field, when AFP was added at 0.35 μM. In the samples containing AFP fluorescence had been increased on the aluminum electrode due to negative dielectrophoretic forces during applying the electric field, whereas in the sample containing no AFP, found no change in images was found before and during applying the electric field. These images were processed with Scion Image to obtain densitograms of the band regions where in fluorescence was increased, and the increased amount of fluorescence was expressed as image output concentration values. FIG. 10 shows the relationship between the AFP concentrations and the increased amounts of fluorescence.

From results of FIG. 10, it will be understood that a good dose response is found between the added AFP concentrations and the image output concentration values and that AFP can be detected quantitatively.

2-2 Detection of AFP in Serum (Reagents)

The same reagents as those in 2-1 were used.

Reaction:

After samples having the components as shown in Table 2 were prepared with normal serum containing no AFP, the antigen-antibody reaction was carried out by allowing standing for two hours at room temperature.

After the antigen-antibody reaction was completed, the reaction solutions were diluted to 100 times with distilled water to and the resultants were subjected to dielectrophoresis.

(Procedures)

Procedures were carried out similarly to those in 2-1.

(Results)

Figure 11:
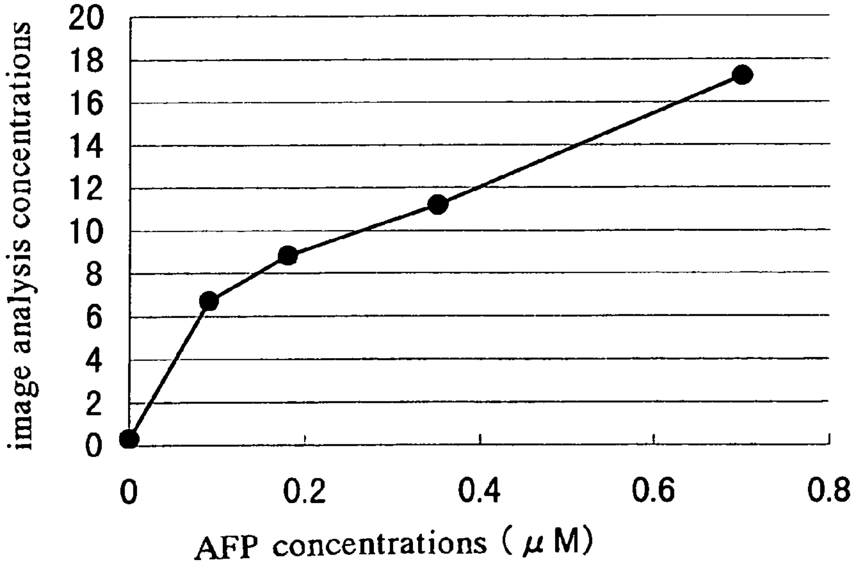
FIG. 11 is a graph showing the relationship between AFP concentrations in serum and image analysis concentrations obtained in Example 2

The results are shown in FIG. 11. It can be found from FIG. 11 that a good quantitativeness is obtained within the range of the presence of AFP. From this finding, it is understood that, if serum is used as samples, components in the serum do not affect dielectrophoresis to a great extent, and the detection of a protein to be measured in serum can be achieved.

From these results, the use of a substance having negative dielectrophoresis, like latex beads, as a separation improving substance allows separating on the dielectrophoretic electrode a biological component having positive dielectrophoresis, and will have permitted to quantitatively separate and detect a protein at the molecular level, which is impossible until now.

Example 3

Detection of λDNA with Probe DNA Bound Latex Beads as a Separation Improving Substance (Reagents)

Preparation of 2 kb DNA probe immobilized latex beads:

In order to prepare streptavidin beads for fixing a probe DNA, streptavidin was immobilized on carboxylated latex beads with a diameter of 2 μm (Polysciences, Inc.), using Carbodiimide Kit for Carboxylated Microparticles (Polysciences, Inc.). As the probe DNA was used a product obtained by amplifying 2 kb of an almost middle sequence of λDNA by PCR using a 5'-biotin-labeled 5'-CTATGACTGTACGCCACTGTCC-3' primer and a 5'-CAATCACCAACCCAGAAAACAATG-3' primer. The product was reacted with the streptavidin-immobilized, beads to prepare 2 kb DNA immobilized latex beads.

The prepared 2 kb DNA immobilized latex beads were kept standing in 0.3 N NaOH for 5 minutes to denature the 2 kb DNA to single strands. After the beads were precipitated by centrifugation, the beads were re-suspended in 0.3 N NaOH. HCl solution was added to the final concentration of 0.3 N for neutralization to make 2 kb DNA probe immobilized latex beads.

Labeling and denaturing to single strands of λDNA and T7 DNA:

Lambda DNA and T7 DNA having a different sequence from λDNA were labeled with fluorescein (green fluorescence) and Cy3 (red fluorescence; Molecular Probes, Inc.), respectively, using Label IT Nucleic Acid Labeling Kit. The labeled DNAs were denatured to single strands by allowing them standing at room temperature for 5 minutes in 0.3N NaOH, and then neutralized by adding MCI solution to the final concentration of 0.3 N.

Hybridization Reaction:

In SSC buffer, 0.05% (w/v) of the 2 kb λDNA probe immobilized latex beads was added to the labeled singled-stranded λDNA and T7 DNA to the final concentration of 20 μg/ml, and hybridization was carried out at 68° C. for 18 hours. The sample solution after the hybridization reaction was diluted 100 times with distilled water, and subjected to dielectrophoresis.

(Procedures)

Procedures were carried out similarly to those in 2-1, except for employing the electric field having a frequency of 3 MHz and an electric field strength of 0.9 MV/m.

(Results)

Figure 12:
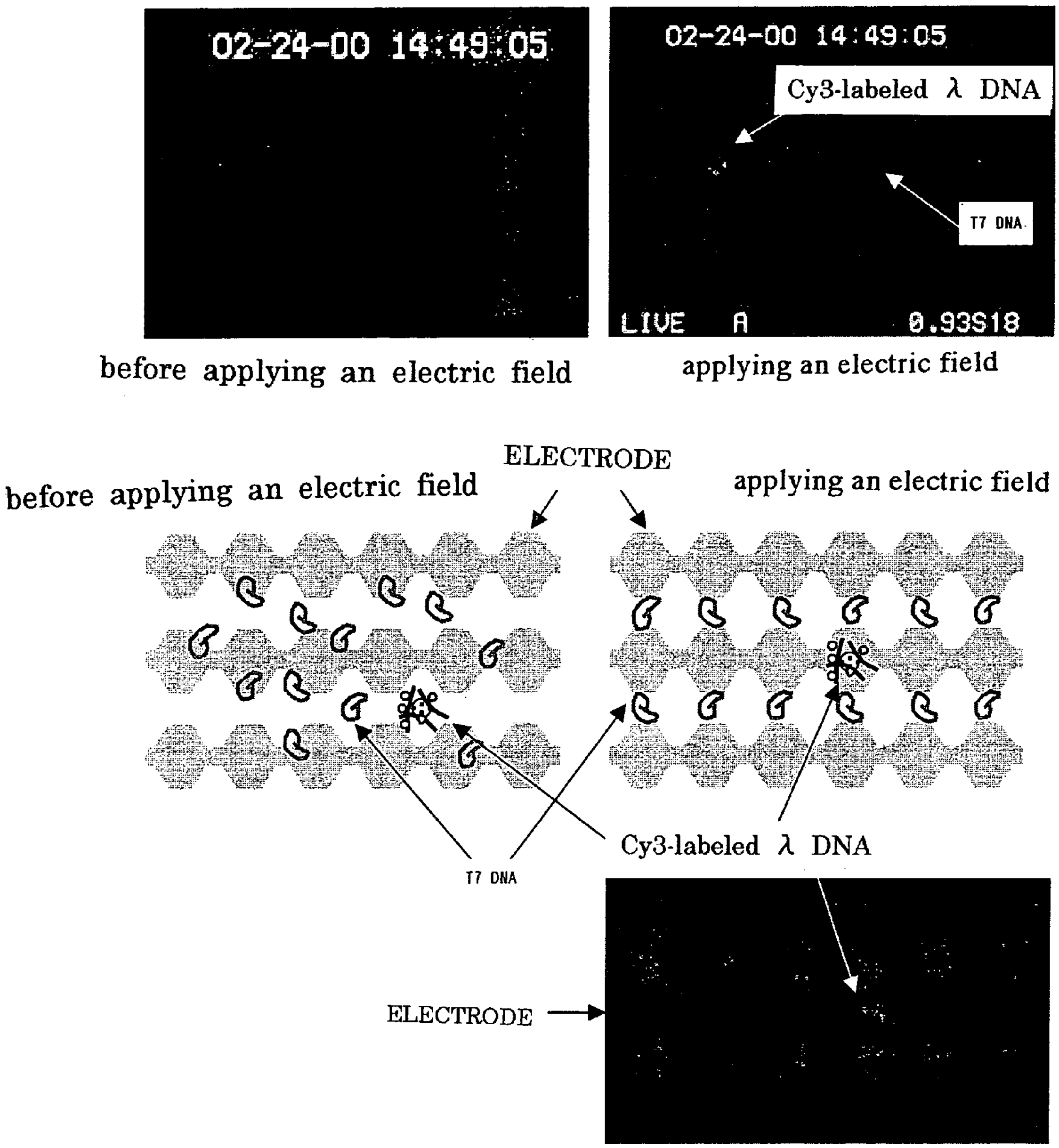
FIG. 12 is a schematic view of electrode before and during applying an electric field and a fluorescence microscope photographs during applying an electric field obtained in Example 3.

The results are shown in FIG. 12.

When the solution after hybridization was observed under a fluorescence microscope, only the fluorescence of Cy3 with which the λDNA was labeled was observed on the beads. When the electric field was applied after this solution was dropped onto the dielectrophoretic electrode, the latex beads received negative dielectrophoretic forces and moved to a weak region in the electric field strength, so that the fluorescence of Cy3-labeled λDNA bound to the 2 kbDNA probe bound beads was observed at a weak region in a weak electric field strength. In contrast, the fluorescence of fluorescein-labeled T7 DNA not bound to the 2 kb DNA probe immobilized beads was observed at an edge region of the electrode, due to movement to a strong region in the electric field strength by positive dielectrophoresis. This Example thus demonstrates that the use of latex beads as a dielectrophoretic separation improving substance will permit to separate and detect a specific DNA molecule among a lot of molecular species.

From these results, it is understood that a dielectrophoretic separation improving substance is useful in dielectrophoretic separation for the detection of a substance.

Experimental Example 1

Observation of Molecules on the Electrode (1) Observation of DNA Molecules

As DNA samples were used 1 ml of a ultrapure water solution containing 0.001 mg λDNA (48.5 kb, double stranded), which was labeled with a fluorescent reagent YO-PRO-1 (a trade name of Molecular Probes, Inc.) according to the method described in R. P. Hogland, Handbook of Fluorescent Probes and Research Chemicals, 6th Edition, Molecular Probes, Inc. (1996), and 1 ml of a ultrapure water solution containing 0.002 mg of an oligonucleotide (22 bases, single stranded DNA, prepared by the inventors), which was labeled at the terminal with a fluorescent dye fluorescein when synthesized as a short DNA by a usual method, respectively.

In order to examine whether or not DNA molecules undergo dielectrophoresis on the electrode substrate manufactured in Reference Example 1, 10 μl of the respective DNA samples described above (the labeled λDNA and oligonucleotide) was dropped onto the electrode substrate, and the fluorescence of the DNA samples was observed under a fluorescence microscope by gradually applying to the electrode an AC voltage with a frequency of 1 MHz.

It was observed that the λDNA began to gather to a strong electric field position by dielectrophoresis at about 500 kV/m of the electric field strength on the minimum gap between the electrodes. At this electric field strength, however, it was not observed that the oligonucleotide gathered to a strong electric field position by dielectrophoresis.

(2) Observation of Protein Molecules

As protein samples were used a ultrapure water solution containing 0.1 mg of IgM (molecular weight, about 900 kDa), which was labeled with a fluorescent reagent FITC (fluorescein isothiocyanate, Wako Pure Chemicals Industries, Ltd.) according to the method described in H. Maeda, Journal of Biochemistry, 65, 777 (1969), and a ultrapure water solution containing 0.1 mg of BSA (molecular weight, about 65 kDa), which was labeled with a fluorescent reagent TRITC (tetramethylrhodamine isothiocyanate, Wako Pure Chemicals Industries, Ltd.) according to the method described in H. Maeda, Journal of Biochemistry, 65, 777 (1969), respectively.

In order to examine whether or not protein molecules undergo dielectrophoresis on the electrode substrate, 10 μl of the respective protein samples described above (the labeled IgM and BSA) was dropped onto the electrode substrate, and the fluorescence of the DNA samples was observed under a fluorescence microscope by gradually applying to the electrode an AC voltage with a frequency of 1 MHz.

It was observed that the FITC-labeled IgM began to gather to a strong electric field position at about 1.0 MV/m of the electric field strength on the minimum gap in the electrode. At this electric field strength, however, it was barely observed that the TRITC-labeled BSA gathered to a strong electric field position by dielectrophoresis.

Experimental Example 2

Analysis of Molecules with the Electrode Substrate Having a Flow Path (Reagents)

As molecule samples were used the labeled λDNA and oligonucleotide solutions used in Experimental Example 1.

(Procedures)

The molecule solutions described above were fed to the electrode substrate having the flow path manufactured in Reference Example 2 at a flow rate of 800 ìm/sec at the sample injection port using a microsyringe pump (KSD 100, Aishisu Co., Inc.). The applied electric field had a frequency of 1 MHz and electric field strengths of a few hundreds kV/m to a few MV/m (defined as the applied voltage/7 μm of the minimum gap).

The each molecule sample (10 μg/ml of the labeled λDNA or 0.56 pg/ml of the labeled oligonucleotide) was introduced at the sample injection port on the electrode substrate, and the amount of fluorescence was measured near the flow path outlet with applying the predetermined electric field for a period of 30 to 80 seconds after introducing each sample.

Measurements were carried out by taking fluorescent images every about five seconds at the flow path near the outlet of the flow path using a confocal laser microscope (LSM-GB 200, Olympus Optical Co., Ltd.) and calculating the sum of brightness values of all the pixels (hereinafter referred to the fluorescence amount). In the measurements, when perfect confocal images are used, in the case where the distribution of fluorescent intensity takes place with the depth of the flow path, accurate results are not obtained. Thus, the orifice on the photomultiplier of the laser microscope was opened fully so as to permit to integrate and measure the fluorescence depending on the depth as well.

The capture ratio was calculated from the above-described equation 1.

In these measurements, when the electric field is not applied, the fluorescence amount measured at the electrode outlet is equal to that at the inlet, since samples of fluorescence-labeled molecule move on the electrode structure by means of the syringe pump. However, when the electric field is applied and molecules are attracted to the electrode by dielectrophoretic forces, the fluorescence amount will be decreased. Therefore, the decreased amount in the fluorescence amount is taken as the captured amount of molecules and used to indicate the amount of molecules attracted to the electrode when the total amount of the initial molecules is consider to be 100.

(Results)

Figure 13:
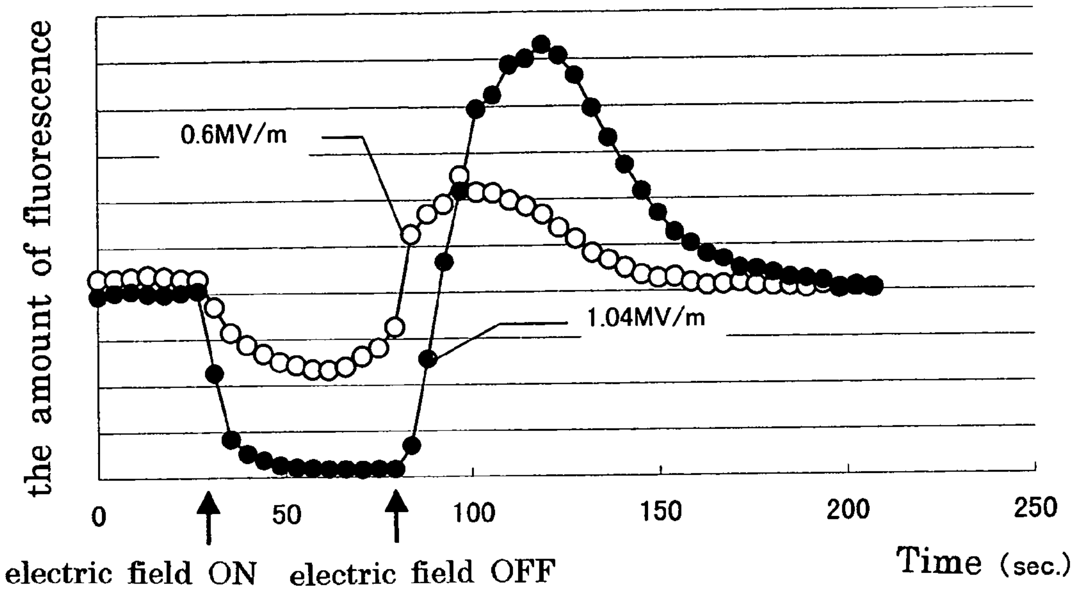
FIG. 13 is a graph showing changes over time of the amount of fluorescence at the outlet of the flow path obtained by using a labeled λ DNA solution in Experimental Example 2.
Figure 14:
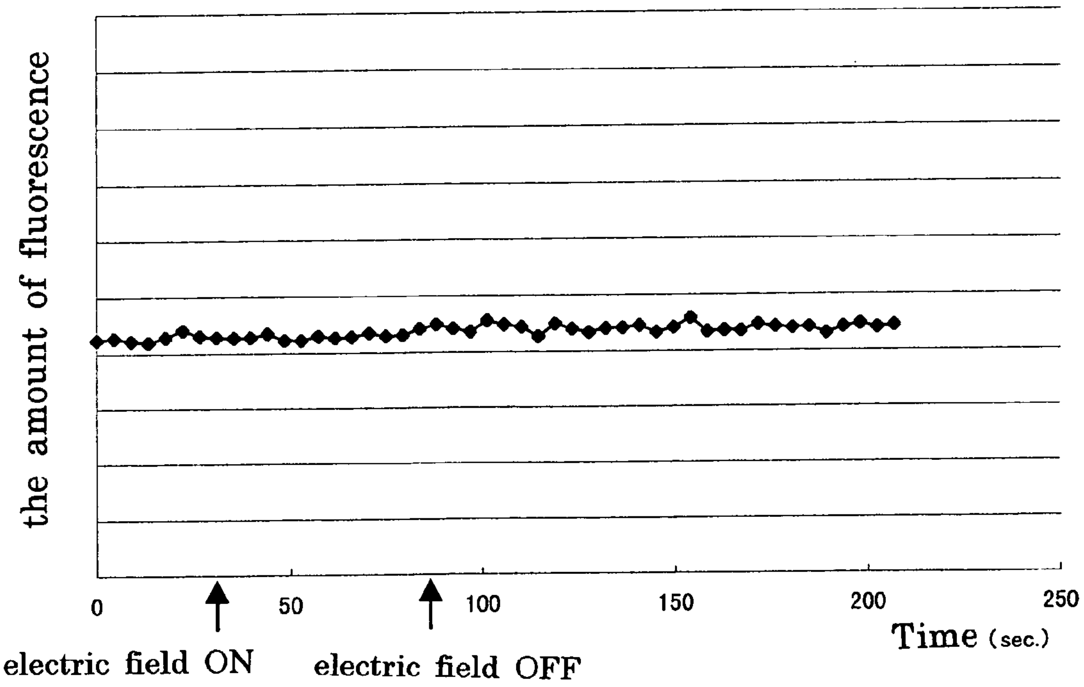
FIG. 14 is a graph showing changes over time of the amount of fluorescence at the outlet of the flow path obtained by using a labeled oligonucleotide solution in Experimental Example 2.

FIG. 13 shows the time course of the fluorescence amount at the outlet of the flow path when the labeled λDNA solution was used and the applied electric field had an electric field strength of 0.60 or 1.04 MV/m. FIG. 14 shows the time course of the fluorescence amount at the outlet of the flow path when the labeled oligonucleotide solution was used and the applied electric field had an electric field strength of 1.4 MV/m. In FIG. 13, results under the applied electric field strength of 0.60 MV/m are indicated by open circles, and results under 1.04 MV/m by closed circles.

As shown in FIG. 13, it is recognized that when the labeled λDNA solution was used and the applied electric field had an electric field strength of 1.04 MV/m, the fluorescence amount at the outlet of the flow path was reduced to approximately zero since the electric field was sufficiently strong and all the λDNA were captured at the electrode. A transient increase in the fluorescence amount after 80 seconds is due to ceasing the electric field, resulting in releasing the DNA molecules which had been accumulated at the electrode until then, and thereby transiently giving a larger fluorescence amount than that at the initial state. After the captured DNA had been released, the fluorescence amount was returned to the initial level. A similar pattern can be also recognized when the labeled λDNA solution was used and the applied electric field had an electric field strength of 0.60 MV/m. However, it is understood that the fluorescence amount was not reduced to zero during applying the electric field (for the period of 30 to 80 seconds), in other words, the DNA was not captured completely since the electric field strength was not sufficient. Additionally, although the λ DNA was strongly captured at a strong electric field position at an electric field strength of 0.5 MV/m in Experimental Example 1, it is understood in these experiments that when a similar ability to capture DNA on the electrode is to be obtained, it is necessary to provide a stronger electric field strength than that without the flowing in the flow path, because the drag resulting from the flowing is added.

As shown in FIG. 14, it is understood that, when the labeled oligonucleotide solution was used and the applied electric field had an electric field strength of 1.4 MV/m, no decrease in the fluorescence amount was observed, that is, the labeled oligonucleotide was not captured at this electric field strength at all.

These results suggest that λDNA and an oligonucleotide can be separated each other by using the separation method of the present invention.

Example 4

Separation of DNA Molecules in Solutions

The respective components were separated from solutions in which λDNA (48.5 kb, double stranded) and an oligonucleotide (22 bases, single stranded DNA).

(Samples)

Preliminary measurements of fluorescence intensity were carried out to confirm that 5 μg/ml of λDNA (48.5 kb, double stranded) labeled with a fluorescent reagent YO-PRO-1 and 2.3 pg/ml of an oligonucleotide (22 bases, single stranded DNA) labeled with a fluorescent reagent fluorescein at the terminal in the synthesis as a short chain DNA emit the same amount of fluorescence each other. As samples were used ultrapure water solutions containing the labeled oligonucleotide and the labeled λDNA at given concentrations as shown in the following table 3, based on this result. Table 3

| Sample No. | Mixing ratio oligonucleotide:ë DNA | Concentration labeled oligonucleotide | Concentration labeled ë DNA |
|---|---|---|---|
| 1 | 0:1 | 0 pg/ml | 10 μg/ml |
| 2 | 1:1 | 2.3 pg/ml | 5 μg/ml |

-continued

| Sample No. | Mixing ratio oligonucleotide:ë DNA | Concentration labeled oligonucleotide | Concentration labeled ë DNA |
|---|---|---|---|
| 3 | 5:1 | 2.3 pg/ml | 1 μg/ml |
| 4 | 1:0 | 2.3 pg/ml | 0 μg/ml |

(Procedures)

The samples were fed to the electrode substrate having the flow path manufactured in Reference Example 2 at a flow rate of 800 μm/sec at the sample injection port using a microsyringe pump (KSD 100, Aishisu Co., Inc.). The applied electric field had a frequency of 1 MHz and an electric field strength of 0.86 MV/m or 1.02 MV/m, and the predetermined electric field was applied for the period of 30 to 80 seconds after sample injection to measure the fluorescence amounts of the labeled λDNA near the outlet of the flow path. Measurements and the determination of the capture ratio were carried out as in Experimental Example 2.

(Results)

Figure 15:
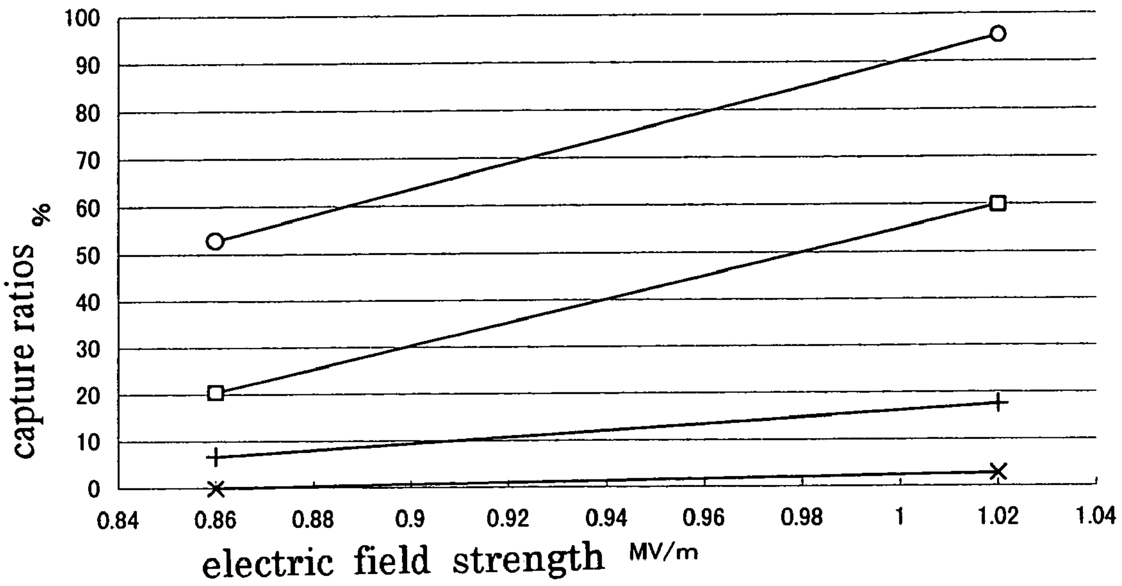
FIG. 15 is a graph showing the relationship between the electric field strengths and the capture ratios of a labeled λDNA obtained in Example 4.

The results are shown in FIG. 15, in which the results from the sample having a mixing ratio of 0:1 of the labeled oligonucleotide and λDNA is indicated by open circles, the results from the sample having a mixing ratio of 1:1 by open squares, the results from the sample having a mixing ratio of 5:1 by +, and the results from the sample having a mixing ratio of 1:0 by x.

In this Example, taking account of the event where all the λDNA are captured and the oligonucleotide is not captured at all, the capture ratio is equal to the percentage of the fluorescence amount derived from the λDNA occupied in the fluorescence amount of a whole sample. That is, Sample 1 (a sample having a mixing ratio of 0:1 of the labeled oligonucleotide and λDNA) should give a capture ratio of 100%, Sample 2 (a sample having a mixing ratio of 1:1 of the labeled oligonucleotide and λDNA) should give a capture ratio of 1/(1+1)=50%, Sample 3 (a sample having a mixing ratio of 5:1 of the labeled oligonucleotide and λDNA) should give a capture ratio of 1/(1+5)=16.7%, and Sample 4 (a sample having a mixing ratio of 1:0 of the labeled oligonucleotide and λDNA) should give a capture ratio of 0%.

From the results shown in FIG. 15, it is understood that, when the applied electric field had an electric field strength of 0.86 MV/m, the capture ratio of the λDNA (Sample 1) was 53% and the oligonucleotide (Sample 4) was not captured at all. Additionally, for Sample 2 (a sample of λDNA to oligonucleotide=1:1), the obtained capture ratio was half the above-mentioned value, a little more than 20%, and for Sample 3 (a sample of λDNA to oligonucleotide=1:5), the obtained capture ratio was a little less than 10%. It is understood that these capture ratios are almost consistent with the theoretical values calculated from 53% of the capture ratio of Sample 1 (Sample 2, 53% ÷1/(1+1)=26.5%; Sample 3, 53%÷1/(1 +5)=8.8%).

When the applied electric field had an electric field strength of 1.02 MV/m, it is understood that 100% of the capture ratio was obtained for the λDNA alone (Sample 1) and no capture was obtained for the oligonucleotide alone (Sample 4). It is also understood that Sample 2 gave a capture ratio of 60% and Sample 3 gave a capture ratio of about 20%, and these capture ratios are almost consistent with the respective theoretical values, 50% and 16.7%. It is understood from these that λDNA and an oligonucleotide can be separated each other in a short time of a few ten seconds according to the method of the present invention.

It is understood from these results that two or more kinds of molecule can be separated each other with combinations of a molecule to be separated and co-existing molecule(s) by selecting an appropriate strength of the electric field.

Example 5

Separation of Protein Molecules in Solutions

The respective components were separated from solutions in which IgM (molecular weight, about 900 kDa) and BSA (molecular weight, about 65 kDa).

(Samples)

As samples were used superpure water solutions containing 0.1 mg/ml of IgM (molecular weight, about 900 kDa) labeled with a fluorescent reagent FITC and 0.1 mg/ml of BSA (molecular weight, about 65 kDa) labeled with a fluorescent reagent TRITC.

(Procedures)

Procedures were carried out similarly to those in Example 1, except for employing a flow rate of 400 μm/sec and an applied electric field strength of 1.42, 1.78, or 2.14 MV/m, and the fluorescence amounts of the labeled IgM and BSA were simultaneously measured to determine the respective capture ratios.

(Results)

Figure 16:
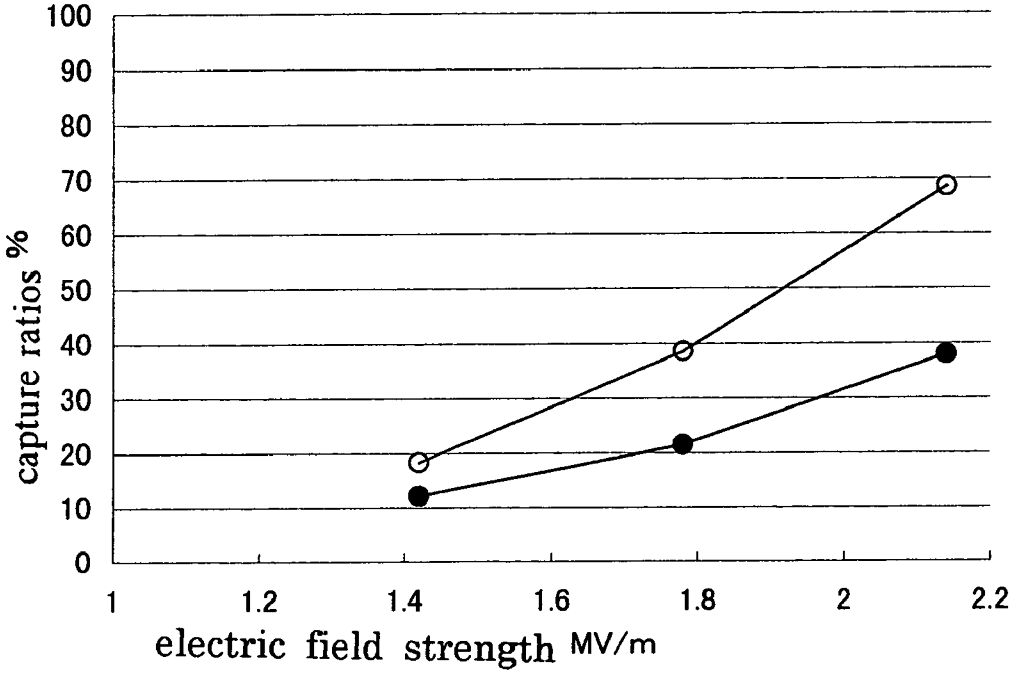
FIG. 16 is a graph showing the relationship between the electric field strengths and the capture ratios of a labeled IgM or a labeled BSA obtained in Example 5.

The results are shown in FIG. 16, in which the capture ratios of the labeled IgM and BSA are indicated by open circles and closed circles, respectively.

From the results shown in FIG. 16, it is understood that for both IgM and BSA, the capture ratio was increased with increasing electric field strengths, and at an electric field strength of 2.14 MV/m, the capture ratio was about 68.5% for IgM and 38% for BSA, and thus there is a clear difference in capture ratio according to the difference in molecular weight.

Although the protein molecules were not able to be captured completely at the electric field strength employed in this Example, it is readily expected that the separation of IgM from BSA can be achieved by further extending the separation region of the electrode, since a significant difference in the capture ratio is found according to the difference in molecular weight. This suggests that the method of the present invention allows separation also according to the difference in the size on the molecular level of proteins.

Example 6

B/F Separation after Antigen-Antibody Reaction

Biotin-labeled λDNA/fluorescein-labeled anti-biotin antibody complex molecules and free fluorescein-labeled anti-biotin antibody not bound to biotin-labeled λDNA were separated each other from solutions obtained by mixing biotin-labeled λDNA and fluorescein-labeled anti-biotin antibody, followed by the antigen-antibody reaction.

(Samples)

Biotin-labeled λDNA was prepared with Photo-Biotin Labeling Kit (Nippon Gene Co., Ltd.) according to the appended preparing protocol, and then the components were mixed in 50 mM PBS (pH 7.5) at ratios as shown in Table 4 to carry out the antigen-antibody reaction. After the antigen-antibody reaction was completed, the medium was substituted with 2.5 mM carbonate buffer (pH 10) using an ultra-filtration filter having a cut-off molecular weight of 50000 to make samples.

The concentration of 21 μg/ml fluorescein-labeled anti-biotin antibody (Cosmo Bio Co. Ltd.) has biotin moles equal to those in 10 μg/ml biotin-labeled λDNA.

TABLE 4

| Sample No. | Concentration Biotin-labeled λ DNA | Concentration Fluorescein-labeled anti-biotin antibody | Concentration unlabeled λ DNA |
|---|---|---|---|
| 1 | 0 μg/ml | 21 μg/ml | 10 μg/ml |
| 2 | 2.5 μg/ml | 21 μg/ml | 7.5 μg/ml |
| 3 | 5 μg/ml | 21 μg/ml | 5 μg/ml |
| 4 | 10 μ/ml | 21 μg/ml | 0 μg/ml |

(Procedures)

The electric field strength was 1.07 MV/m and procedures were carried out at similarly to those in Example 2. The fluorescence amounts of the fluorescein-labeled anti-biotin antibody in the complex molecules and the free fluorescein-labeled anti-biotin antibody were measured to determine the capture ratio.

(Results)

Figure 17:
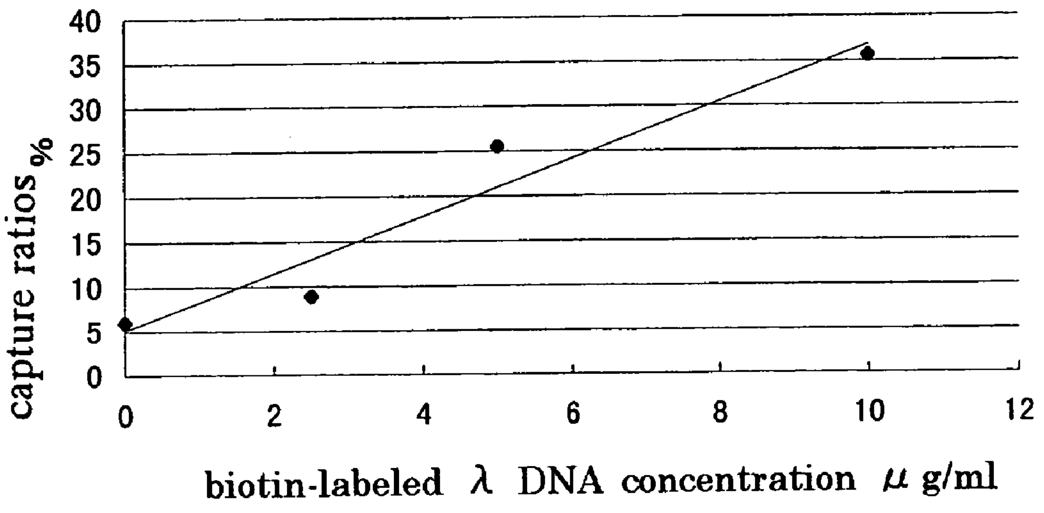
FIG. 17 is a graph showing the relationship between biotin-labeled λDNA concentrations and the capture ratios obtained in Example 6.

The results are shown in FIG. 17. As shown from the results in FIG. 17, it is understood that the capture ratio of the complex molecule was 36% for a biotin-λDNA concentration of 10 μg/ml, 25% for 5 μg/ml, 8.9% for 2.5 μg/ml, and 6% for 0 μg/ml, and thus the capture ratio is decreased with decreasing concentrations of biotin-labeled λDNA. Under sufficient dielectrophoretic conditions for capturing the λDNA at 100%, when unlabeled λDNA of Sample 1 was applied, the capture ratio was 6%, whereas applying labeled λDNAs of Samples 2, 3, and 4 gave a significantly higher capture ratio. Therefore, it is understood that the separation of complex molecules resulting from the antigen-antibody reaction of fluorescein-labeled anti-biotin antibody and biotin-labeled λDNA from free fluorescein-labeled anti-biotin antibody not bound to biotin-labeled ë DNA can be performed with somewhat concentration dependency.

ADVANTAGEOUS EFFECT OF THE INVENTION

As mentioned above, according to the first method of the present invention, two or more kinds of molecules dissolved in a solution which have not allowed separation until now have been successfully separated from one another for the first time with dielectrophoretic forces by a method of forming a complex substance containing a separation improving substance, which have not been carried out in the past. Thus, the present invention is a very breakthrough invention.

Additionally, the second method of the present invention is the first method by which two or more kinds of molecules dissolved in a solution which have not allowed separation until now have been successfully separated from one another using dielectrophoretic forces under a strong electric field which have not been employed in the past.

According to the present invention, the respective molecules can be rapidly and readily separated from a solution in which are dissolved two or more kinds of molecules, such as biological component molecules, for example, DNAs and proteins, which have not allowed separation by dielectrophoretic forces until now.

What is claimed is:

1. A method for separating two or more kinds of molecules dissolved in a sample by a dielectrophoretic force, comprising:

forming a reaction mixture containing a complex substance of a specific molecule of said two or more kinds of molecules in a sample and a substance capable of changing dielectrophoretic properties of the specific molecule, which binds to the specific molecule, and subjecting the resulting reaction mixture containing the complex substance to application of dielectrophoresis using a nonuniform electric field generated by supplying only one kind of voltage, which is either an AC electric field or a DC electric field having an electric field strength of 500 kV/m to 10 MV/m which is formed by electrodes which are made of conductive material, and separating the complex substance from molecules other than the specific molecule in the sample.

2. A method for determining an amount of a component in a sample, comprising:

forming a reaction mixture containing a complex substance of a specific molecule of two or more kinds of molecules in a sample and a substance capable of changing dielectrophoretic properties of the specific molecule which binds to the specific molecule, subjecting the resulting reaction mixture containing the complex substance to application of dielectrophoresis using a nonuniform electric field generated by supplying only one kind of voltage, which is either an AC electric field or a DC electric field having an electric field strength of 500 kV/m to 10 MV/m which is formed by electrodes which are made of conductive material, separating the complex substance from molecules other than the specific molecule, measuring the specific molecule in the separated complex substance or a molecule other than the specific molecule in the sample, and determining the amount of the component in the sample on the basis of the measurement result.

3. The method according to claim 2, wherein each of the component and the specific molecule is a molecule to be measured.

4. A method for separating a complex substance of a specific molecule of two or more kinds of molecules in a sample, a substance binding to the specific molecule and a substance capable of changing dielectrophoretic properties of the specific molecule which binds to the specific molecule from the substance binding to the specific molecule which is not involved in forming the complex substance, comprising:

contacting the sample containing the specific molecule with the substance binding to the specific molecule, and the substance capable of changing dielectrophoretic properties of the specific molecule to form a reaction mixture containing the complex substance, and subjecting the resulting reaction mixture containing the complex substance to the application of dielectrophoresis using a nonuniform electric field generated by supplying only one kind of voltage, which is either an AC electric field or a DC electric field having an electric field strength of 500 kV/m to 10 MV/m which is formed by electrodes which are made of conductive material, and separating the complex substance from the substance binding to the specific molecule which is not involved in forming the complex substance.

5. A method for detecting a specific molecule of two or more kinds of molecules in a sample, comprising:

contacting a sample containing a specific molecule with a substance binding to the specific molecule, and a substance capable of changing dielectrophoretic properties of the specific molecule which binds to the specific molecule to form a reaction mixture containing a complex substance of the specific molecule, the substance binding to the specific molecule, and the substance capable of changing dielectrophoretic properties of the specific molecule, subjecting the resulting reaction mixture containing the complex substance to the application of dielectrophoresis using a nonuniform electric field generated by supplying only one kind of voltage, which is either an AC electric field or a DC electric field having an electric field strength of 500 kV/m to 10 MV/m which is formed by electrodes which are made of conductive material, separating the complex substance from the substance binding to the specific molecule which is not involved in forming the complex substance, measuring the substance binding to the specific molecule in the separated complex substance, and detecting the presence or absence of the specific molecule in the sample on the basis of the measurement result.

6. A method for determining an amount of a component in a sample, comprising:

contacting a sample containing a specific molecule of two or more kinds of molecules with a substance binding to the specific molecule and a substance capable of changing dielectrophoretic properties of the specific molecule which binds to the specific molecule to form a reaction mixture of a complex substance of the specific molecule and the substance capable of changing dielectrophoretic properties of the specific molecule, subjecting the resulting reaction mixture containing the complex substance to the application of dielectrophoresis using a nonuniform electric field generated by supplying only one kind of voltage, which is either an AC electric field or a DC electric field having an electric field strength of 500 kV/m or to 10 MV/m which is formed by electrodes which are made of conductive material, separating the complex substance from the substance binding to the specific molecule which is not involved in forming the complex substance, measuring the specific molecule or the substance binding to the specific molecule in the separated complex substance or the substance binding to the specific molecule which is not involved in forming the complex substance, and determining the amount of the component in the sample on the basis of the measurement result.

7. A method for determining an amount of a component in a sample, comprising:

contacting a sample containing a specific molecule of two or more kinds of molecules with a specific molecule labeled by a labeling substance, and a substance capable of changing dielectrophoretic properties of the specific molecule which binds to the specific molecule to form a reaction mixture containing a labeled complex substance of the specific molecule labeled by the labeling substance and the substance capable of changing dielectrophoretic properties of the specific molecule, subjecting the resulting reaction mixture containing the labeled complex substance to the application of dielectrophoresis using a nonuniform electric field generated by supplying only one kind of voltage, which is either an AC electric field or a DC electric field having an electric field strength of 500 kV/m to 10 MV/m which is formed by electrodes which are made of conductive material, separating the labeled complex substance from the specific molecule labeled by the labeling substance which is not involved in forming the complex substance, measuring the specific molecule labeled by the labeling substance in the separated labeled complex substance or the specific molecule labeled by the labeling substance which is not involved in forming the complex substance, and determining the amount of the component in the sample on the basis of the measurement result.

8. The method according to any one of claims 1 to 7, wherein the sample containing the specific molecule is a sample derived from a living body, or a treated material of the body-derived sample.

9. The method according to any one of claims 1, 2, 4, 5 and 7, wherein the substance capable of changing dielectrophoretic properties of the specific molecule is a substance which can give to the specific molecule dielectrophoretic properties, on the basis of which the specific molecule can be separated from molecules other than the specific molecule contained in the sample by dielectrophoresis, by binding the specific molecule.

10. The method according to any one of claims 4, 5 and 6, wherein the sample containing the specific molecule is a sample derived from a living body, or a treated material of the body-derived sample, wherein the substance capable of changing dielectrophoretic properties of the specific molecule is a substance which can give to the specific molecule dielectrophoretic properties, on the basis of which the specific molecule can be separated from molecules other than the specific molecule contained in the sample by dielectrophoresis, by binding the specific molecule, and wherein the substance binding to the specific molecule is a substance which binds to the specific molecule by an antigen-antibody reaction, a sugar chain-lectin reaction, an enzyme-inhibitor reaction, a protein-peptide chain reaction, a chromosome or nucleotide chain-nucleotide chain reaction.

11. A method according to claim 1, wherein the substance capable of changing dielectrophoretic properties of the specific molecule is one having a size of 1 mm or less, and the nonuniform electric field is one having an electric field strength of 3.5 MV/m or less which is caused by applying an applied frequency of 100 Hz to 10 Hz.

12. A method according to claim 1, wherein the separation of the complex substance from molecules other than the specific molecule by dielectrophoresis is conducted by (i) only dielectrophoretic forces or (ii) only the combination of (a) dielectrophoretic forces and (b) forces selected from group consisting of electrophoretic forces and forces of a solution flow (forces by a mobile phase).

13. A method for separating two or more kinds of molecules from each other, which comprises placing a solution in which the two or more kinds of molecules are dissolved under a nonuniform electric field generated by supplying only one kind of voltage having an electric field strength of 500 KV/m to 10 MV/m, formed by electrodes which have a structure capable of forming a nonuniform electric field and which are made of conductive material.

14. A method for detecting a molecule to be measured in a sample, which comprises:

reacting a liquid sample, in which a molecule to be measured is dissolved, and a solution, in which a substance specifically binding to the molecule to be measured is dissolved, to obtain a solution in which a complex substance of the molecule to be measured and the substance specifically binding to the molecule to be measured, and the substance specifically binding to the molecule to be measured which is not involved in the reaction are dissolved, placing the solution under a nonuniform electric field generated by supplying only one kind of voltage having an electric field strength of 500 KV/m to 10 MV/m, the field being formed by electrodes which have a structure capable of forming a horizontally and vertically ununiform electric field and which are made of conductive material, separating the complex substance from the substance specifically binding to the molecule to be measured which is not involved in the reaction, measuring the substance specifically binding to the molecule to be measured in the complex substance, and detecting the presence or absence of the molecule to be measured in the sample on the basis of the measurement result.

15. A method for measuring a substance to be measured in a sample, which comprises:

reacting a liquid sample, in which a molecule to be measured is dissolved, and a solution, in which a substance specifically binding to the molecule to be measured is dissolved, to obtain a solution in which a complex substance of the molecule to be measured and the substance specifically binding to the molecule to be measured, and the substance specifically binding to the molecule to be measured which is not involved in the reaction are dissolved, placing the solution under a nonuniform electric field generated by supplying only one kind of voltage having an electric field strength of 500 KV/m to 10 MV/m, the field being formed by electrodes which have a structure capable of forming a horizontally and vertically ununiform electric field and which are made of conductive material, separating the complex substance from the substance specifically binding to the molecule to be measured which is not involved in the reaction, and measuring the substance specifically binding to the molecule to be measured in the complex substance, or the substance specifically binding to the molecule to be measured which is not involved in the reaction.

16. A method for measuring a substance to be measured in a sample, comprising:

reacting a liquid sample containing a molecule to be measured, a molecule to be measured labeled by a labeling substance, and a substance specifically binding to the molecule to be measured to obtain a solution containing a complex substance of the molecule to be measured labeled by a labeling substance and the substance specifically binding to the molecule to be measured, a complex substance of the molecule to be measured and the substance specifically binding to the molecule to be measured, and the molecule to be measured labeled by a labeling substance which is not involved in the reaction, placing the obtained solution under a nonuniform electric field generated by supplying only one kind of voltage having an electric field strength of 500 KV/m to 10 MV/m, the field being formed by electrodes which have a structure capable of forming a horizontally and vertically ununiform electric field and which are made of conductive material, separating the complex substance of the molecule to be measured labeled by a labeling substance and the substance specifically binding to the molecule to be measured from the molecule to be measured labeled by a labeling substance which is not involved in forming the complex, and then measuring the molecule to be measured labeled by a labeling substance in the complex substance or the molecule to be measured labeled by a labeling substance which is not involved in forming the complex substance to determine the amount of the molecule to be measured in the sample based on the results.

17. The method according to any one of claims 13 to 15, wherein the solution in which the two or more kinds of molecules are dissolved or the sample containing a molecule to be measured is a sample derived from a living body, or a treated material of the body-derived sample.

18. The method according to any one of claims 14 to 15, wherein the substance specifically binding to the molecule to be measured is a substance which binds to the molecule to be measured by an antigen-antibody reaction, a sugar chain-lectin reaction, an enzyme-inhibitor reaction, a protein-peptide chain reaction, a chromosome or nucleotide chain-nucleotide chain reaction.

19. The method according to any one of claims 14 to 15, wherein any one of the molecule to be measured and the substance specifically binding to the molecule to be measured is a protein, and the other is a peptide chain.

20. The method according to any one of claims 14 to 15, wherein any one of the molecule to be measured and the substance specifically binding to the molecule to be measured is a chromosome or nucleotide chain, and the other is a nucleotide chain, protein, or peptide chain.

21. The method according to any one of claims 14 to 15, wherein any one of the molecule to be measured and the substance specifically binding to the molecule to be measured is a glucide, and the other is a protein or peptide chain.

22. The method according to any one of claims 14 to 15, wherein any one of the molecule to be measured and the substance specifically binding to the molecule to be measured is a lectin, and the other is a sugar chain.

* * * * *